(12) United States Patent
Hechinger

(10) Patent No.: US 6,933,106 B2
(45) Date of Patent: *Aug. 23, 2005

(54) PLATELET IMMUNOGLOBULIN BEAD SUSPENSION AND FLOW CYTOMETRY

(76) Inventor: Mark Hechinger, 700 S. Mentor Ave., Pasadena, CA (US) 91106

(*) Notice: Subject to any disclaimer, the term of this patent is extended or adjusted under 35 U.S.C. 154(b) by 180 days.

This patent is subject to a terminal disclaimer.

(21) Appl. No.: 10/243,515

(22) Filed: Sep. 13, 2002

(65) Prior Publication Data

US 2003/0194818 A1 Oct. 16, 2003

Related U.S. Application Data

(63) Continuation of application No. 09/678,707, filed on Oct. 3, 2000, now abandoned, which is a continuation-in-part of application No. 08/868,591, filed on Jun. 4, 1997, now abandoned, which is a continuation-in-part of application No. 08/404,144, filed on Mar. 13, 1995, now abandoned.

(60) Provisional application No. 60/015,873, filed on Jun. 15, 1996.

(51) Int. Cl.$^7$ .................... G01N 33/53; G01N 33/543
(52) U.S. Cl. ............... 435/4; 435/6; 435/7.1; 435/7.2; 435/7.93; 435/7.94; 435/7.95; 435/40.51; 435/173.4; 435/967; 435/973; 436/10; 436/63; 436/501; 436/506; 436/507; 436/509; 436/513; 436/518; 436/519; 436/523; 436/524; 436/527; 436/528; 436/531; 436/533; 436/534; 436/536; 436/538; 436/546; 436/805; 436/811

(58) Field of Search .............. 435/6, 7.1, 7.2, 435/7.93–95, 967, 973, 173.4, 40.51; 436/10, 507, 513, 518, 523, 524, 527, 533, 501, 534, 506, 509, 528, 531, 546, 805, 519, 811, 536, 538, 63

(56) References Cited

U.S. PATENT DOCUMENTS

| | | | |
|---|---|---|---|
| 6,268,222 B1 * | 7/2001 | Chandler et al. | 436/523 |
| 6,280,618 B2 * | 8/2001 | Watkins et al. | 210/222 |
| 2003/0008410 A1 * | 1/2003 | Hechinger | 436/172 |
| 2003/0032068 A1 * | 2/2003 | Hechinger | 435/7.21 |

OTHER PUBLICATIONS

Greenwalt et al. An enzyme linked antiglobulin test to quantify nanogram quantities of IgG on polystyrene microspheres. Vox Sang. 63 (4) pp. 272–275 (1992).*

Rosenfeld et al., Detection of platelet alloantibodies by flow cytometry. Characterization and Clinical Significance. Am J Clin. Path. 85(2), pp. 207–212 (1986).*

* cited by examiner

Primary Examiner—Chris Chin
Assistant Examiner—KArtic Padmanabhan
(74) Attorney, Agent, or Firm—Colin P. Abrahams

(57) ABSTRACT

Immunoassay methods and apparatus are provided which utilize flow cytometry, coated latex microspheres, and fluorochrome labeled antibodies, to simultaneously detect the presence and amount of one or more analytes in a sample. By combining FALS and fluorescence, it is practical to use beads of several different sizes, colors or shapes, each bead coated with a different analyte, for the simultaneous detection of one or more analytes and of cell components such as platelets in a sample.

7 Claims, 30 Drawing Sheets

FIGURE 1 - BEAD DETECTION SYSTEM

Fig. 5 Microspheres of different sizes (4,5,6,7, and 10 μm) as seen with flow cytometer forward and side (90°) light scatter.

Fig. 6  Antigen labeled microspheres incubated with negative serum.

Fig. 7 Antigen labeled microspheres incubated with a serum containing antibody to Scl-70 but negative for antibodies to the four other antigens.

Fig. 8  Multi-color Bead Analysis using size and fluorescense

Fig 9   Schematic presentation illustrating combination of different bead sizes with two different fluorochromes for two color flow cytometry. Differences in bead sizes not shown, but would be seen in three dimensional plot.

Fig. 10 - Clinical Bead Trials - Sensitivity Graph with Mean
Channel Fluorescence in EU/mL Positive Serum Dilutions

| Antigens | | 1:1 | 1:2 | 1:4 | 1:8 | 1:16 | 1:32 | 1:64 | 1:128 |
|---|---|---|---|---|---|---|---|---|---|
| | RNP | 82.6 | 100.2 | 118.9 | 136.3 | 131.5 | 164.8 | 208.3 | 186.9 |
| | | 95.0 | 47.5 | 23.8 | 11.9 | 5.9 | 2.9 | 1.5 | 0.8 |
| | SM | 86.0 | 100.6 | 125.5 | 137.6 | 158.4 | 197.5 | 197.3 | 177.9 |
| | | 100.0 | 50.0 | 25.0 | 12.5 | 6.3 | 3.2 | 1.6 | 0.8 |
| | SSA | 77.4 | 79.8 | 89.0 | 96.2 | 112.4 | 124.1 | 155.6 | 195.3 |
| | | 80.0 | 40.0 | 20.0 | 10.0 | 5.0 | 2.5 | 1.3 | 0.7 |
| | SSB | 54.8 | 64.4 | 70.4 | 76.7 | 86.5 | 105.3 | 120.5 | 155.0 |
| | | 80.0 | 40.0 | 20.0 | 10.0 | 5.0 | 2.5 | 1.3 | 0.7 |
| | SCL-70 | 72.6 | 90.5 | 97.8 | 107.4 | 111.0 | 127.8 | 164.9 | 151.9 |
| | | 110.0 | 55.0 | 27.5 | 13.8 | 6.9 | 3.5 | 1.8 | 0.9 |
| | RNP | SM | SSA | SSB | SCL-70 | | | | |

RHEUMO-BEADS – RNP COMPARISON

RHEUMO-BEADS – SS-B COMPARISON

Sample    : CONTROL MIX    001
Cytometer: FACSCAN
Fl1       : CT              FL2:              FL3 :

FSC  43.255
SSC  23.255
FL1   0.255
FL2   0.255

1  Min
2
5
15

Sample    : CONTROL MIX    001
Cytometer: FACSCAN
Fl1       : CT              FL2:              FL3 :

Contour statistics

Sample    : CONTROL MIX    001
Parameters : FL1  FSC       Gated events :  9979        Total events :  10000

| # | X & Y Lower | X & Y Upper | Events | % Gated | % Tot | X & Y Mean | X & Y Mode | Peak |
|---|---|---|---|---|---|---|---|---|
| 1 | 1.00 / 21 | 18.61 / 63 | 3396 | 34.03 | 33.96 | 3.75 / 33.55 | 2.08 / 26.00 | 160 |
| 2 | 21.54 / 21 | 10000 / 63 | 42 | 0.42 | 0.42 | 29.61 / 46.86 | 21.54 / 33.00 | 4 |
| 3 | 1.00 / 0 | 18.61 / 20 | 6540 | 65.54 | 65.40 | 1.42 / 15.23 | 1.00 / 17.00 | 2143 |
| 4 | 21.54 / 0 | 10000 / 20 | 1 | 0.01 | 0.01 | 80.31 / 13.00 | 80.31 / 13.00 | 1 |
| 5 | 69.39 / 0 | 10000 / 63 | 4 | 0.04 | 0.04 | 84.40 / 43.25 | 69.39 / 63.00 | 1 |
| 6 | 21.54 / 0 | 10000 / 63 | 43 | 0.43 | 0.43 | 30.79 / 46.07 | 21.54 / 33.00 | 4 |

Sample   : MIX BEADS   002
Cytometer: FACSCAN
FL1      : NORMAL CT          FL2:              FL3 :

Contour statistics

Sample    : MIX BEADS   002
Parameters : FL1 FSC       Gated events : 9844        Total events : 10000

| # | X & Y Lower | X & Y Upper | Events | % Gated | % Tot | X & Y Mean | X & Y Mode | Peak |
|---|---|---|---|---|---|---|---|---|
| 1 | 1.00 0 | 10000 63 | 9844 | 100.00 | 98.44 | 4.76 21.33 | 1.00 17.00 | 1827 |
| 2 | 69.39 0 | 10000 63 | 32 | 0.33 | 0.32 | 209.96 49.72 | 69.39 63.00 | 3 |

```
Sample   : MIX BEADS    006
Cytometer: FACSCAN
FL1      : SSB              FL2:              FL3 :
```

```
Sample   : MIX BEADS    006
Cytometer: FACSCAN
FL1      : SSB              FL2:              FL3
                        Contour statistics
Sample    : MIX BEADS    006
Parameters: FL1 FSC        Gated events :  9981      Total events :  10000
```

| # | X & Y Lower | X & Y Upper | Events | % Gated | % Tot | X & Y Mean | X & Y Mode | Peak |
|---|---|---|---|---|---|---|---|---|
| 1 | 1.00 0 | 10000 63 | 9981 | 100.00 | 99.81 | 14.14 21.26 | 1.00 17.00 | 1856 |
| 2 | 69.39 0 | 10000 63 | 140 | 1.40 | 1.40 | 123.05 46.94 | 92.95 57.00 | 5 |

PLATELET IMMUNOGLOBULIN BEAD SUSPENSION AND FLOW CYTOMETRY

CROSS-REFERENCE TO RELATED APPLICATIONS

This application is continuation application of U.S. patent application Ser. No. 09/678,707 filed Oct. 3, 2000 now abandoned, which is a continuation-in-part of U.S. patent application Ser. No. 08/868,591 filed Jun. 4, 1997 now abandoned, which is a continuation-in-part of U.S. patent application Ser. No. 08/404,144, filed Mar. 13, 1995 now abandoned, and which also claims the benefit of U.S. provisional application Ser. No. 60/015,873, filed Jun. 5, 1996. All of the above applications are hereby incorporated by reference.

BACKGROUND OF THE INVENTION

FIELD OF THE INVENTION

The present invention is directed to immunoassay methods and apparatus, and more particularly concerns an immunobead-flow cytometry method, apparatus, assay, device, system, kit, and the like for detecting and quantifying platelets, antigens, antibodies and the like.

Typically, autoimmune testing for Systemic Lupus Erythematosus (SLE), Systemic Rheumatic Disease, rheumatoid arthritis, Sjogren's Syndrome, Progressive Systemic Sclerosis (PSS), Subacute Erythematosus, congenital complete heart block, neonatal complete heart block, neonatal lupus dermatitis, Polymyositis, Human Immunodeficiency Virus (HIV), Acquired Immunodeficiency Syndrome (AIDS), as well as other diseases has involved the use of extractable nuclear antigens (ENA) and immunological assays including hemagglutination, counter immunoelectrophoresis (CIE), immunodiffusion, Enzyme Linked Immunosorbent Assay (ELISA), and the like. For example, the Ro(SS-A) antigen having one major band at 60 kD by SDS gel electrophoresis (silver stain) has been purified through the use of immobilized human anti-Ro(SS-A) immunoglobulins. La(SS-B) antigen has two major bands, one at 40 kD and the other at 23 kD (a degradation product) by SDS gel electrophoresis (silver stain) and has been purified through the use of immobilized human anti-La(SS-B) immunoglobulin. Smith (Sm) antigen has two major bands in the 10 and 14 kD region by SDS gel electrophoresis (silver stain) has been purified through the use of immobilized human anti-Sm (Smith) immunoglobulins. Smith (Sm/RNP) complex antigen has five bands, one each at 70, 40, 24, 12 and 10 kD, respectively, by SDS gel electrophoresis (silver stain) and has been purified through the use of immobilized human anti-RNP immunoglobulin. Scl-70 antigen has one major band at 68 kD by SDS gel electrophoresis (silver stain) and has been purified through the use of immobilized human anti-Scl-70 immunoglobulins. Jo-1 antigen has one major band at 50 kD by SDS gel electrophoresis (silver stain) and has been purified through the use of immobilized human anti-Jo-1 immunoglobulins. dsDNA double-stranded (native) deoxyribonucleic acid, ssDNA single-stranded DNA, whole Histones, Histone subclasses (distinct molecular fractions) tissue extracts, human antibodies, animal tissue acetone powders, sera and immunoglobulin fractions, second antibodies, anti-whole sera, whole antisera to animal proteins and to human proteins have been used in enzyme immunoassay (ELISA) for detecting or evaluating systemic rheumatic diseases. Thus, other antigens may be added to this invention as combined with or separate from the existing 5-bead immunoasay. Immunovision, Inc. of Springdale, Ark. has developed a number of enzyme-linked immunoassays, ouchterlony immunoprecipitation assays, and Western blot assays for detecting human antibody to particular nuclear antigens (ENA).

The presence of human autoantibodies to nuclear antigens, for examples antibodies against RNP/Sm, Sm, SS-A, SS-B, dsDNA and Scl-70 antigens, in combination with IFA, have been diagnostic when evaluating patients with Systemic Lupus Erythematosus (SLE). Positivity may indicate more progressive disease states or simply rheumatoid arthritis. Currently, enzyme linked immunosorbent assay (ELISA) has been the assay of choice to detect these antibodies. Antibodies to Smith (Sm) antigen have been shown to occur in twenty-five to thirty percent of patients with Systemic Lupus Erythematosus. Antibodies to Sm are less commonly found in patients with other rheumatic diseases. Antibodies to ribosomal nuclear protein (nRNP) have been found in patients with Systemic Lupus Erythematosus. They are also found in sera from patients with rheumatoid arthritis, Sjogren's Syndrome (SS), Progressive Systemic Sclerosis (PSS), and Mixed Connective Tissue Disease (MCTD). Twenty to thirty percent of the patients with antibodies to Scl-70 antigen have Progressive Systemic Sclerosis. Antibodies to Scl-70 are rarely found in patients with other systemic rheumatic diseases. Antibodies to Ro (SS-A) antigen are found in half of Systemic Lupus Erythematosus patients, most patients with Sjogren's Syndrome or Subacute Lupus Erythematosus and nearly all mothers of infants with congenital complete heart block or Neonatal Lupus Dermatitis. Antibodies to the La (SS-B) antigen usually occur in twenty to thirty percent of Sjogren's Syndrome patients and with five to ten percent of Systemic Lupus Erythematosus patients. Antibodies to Jo-1 antigen are usually found in patients with polymyositis. Antibodies to Ribosomal P antigens are found to occur in five to ten percent of Systemic Lupus Erythematosus patients and ninety percent of those patients will demonstrate signs of lupus psychosis. Antibodies to mitochondrial antigens are found in all primary biliary cirrhosis patients. Antibodies to histone antigens (H1, H2A, H2B, H3, H4) are found in ninety-five to one-hundred percent of drug-induced Lupus Erythematosus, fifteen to twenty percent rheumatoid arthritis, and thirty percent of all patients with Systemic Lupus Erythematosus. Antibodies to cytoplasmic components of neutrophil granulocytes are present in the serum of patients with acute Wegener's granulomatosis and microscopic polyarteritis. Myeloperoxidase and proteinase 3 are the two major antigens present.

Tan and Peebles in the Manual of Clinical Immunology describe a hemagglutination technique to quantitate antibodies to Sm and RNP. Durata and Tan, using saline-soluble extracts (ENA) from rabbit thymus acetone powder at a concentration of 5 mg protein/mL, demonstrated that increased sensitivity for detecting precipitating antibodies to RNP, Sm, and SS-B could be obtained by using CIE. A modified Ouchterlony technique has been used to show precipitating antibodies to RNA. Immunovision, Inc. has modified and tested the standard procedure for enzyme immunoassays for the detection of autoantibodies using purified antigens.

There are many applications in the field of immunological monitoring in which the presence of body fluid antibodies and antigens are detected by a variety of methods. However, these assays usually measure one antibody or antigen at a time and tend to be time consuming and costly. Latex particles are commonly used clinically for detecting antibodies with agglutination as the end point. U.S. Pat. No. 5,162,863 discloses a method using flow cytometry to detect multiple antigens or antibodies with agglutination of particles combined with light scatter as the end point.

Microsphere based assays using flow cytometry have been reported by several investigators after Horan et al. reported the use of polystyrene microspheres to detect serum rheumatoid factor in 1979.

The merger of bead assays with flow cytometry has been demonstrated in several clinical applications, e.g. detection of antibodies to CMV and herpes simplex; detection of antibodies to different components of the human immunodeficiency virus (HIV);—detection of antibodies to several antigens of Candida albicans; detection of human anti-mouse antibody (HAMA) in transplant patients receiving OKT3; detection of circulating immune complexes and HIV antibody in immune complexes; and detection of two different antibodies to CEA.

Although interest has focused on the detection of antibodies and antigens in fluids the use of other ligand systems and biological probes has been explored, e.g. competitive binding of antibodies to DNA coated beads and detection of viruses. Although the principals and advantages of fluorescent microsphere immunoassays have been discussed in the literatures applications in clinical lab testing have been relatively few despite the economics of time and cost inherent in this technology. Current assays for the autoantibodies seen in several autoimmune disorders are performed individually and require a separate kit for each antibody A method that will simultaneously assay for several different antibodies in one tube would be of significant value.

Also, conventional assays for autoantibodies and the like may provide false positive readings due to background noise caused by platelets or other blood components. A platelet or blood platelet is a component of mammalian blood, and, more particularly, one of the minute protoplasmic disks, about 2 $\mu$m in diameter, occurring in vertebrate blood and playing a role in blood clotting.

Hence, there is a need for an improved immunoassay method and apparatus for detecting and quantifying autoantibodies to nuclear antigens associated with autoimmune diseases as well as for detecting other antigens, antibodies, cell fragments, platelets, viruses, bacteria and the like.

SUMMARY OF THE INVENTION

In accordance with the present invention, immunoassay methods and apparatus are provided which utilize flow cytometry, coated latex microspheres, and fluorochrome labelled antibodies, to simultaneously detect the presence and amount of several antigens or antibodies in a sample.

The use of microspheres, beads, or other particles as solid supports for antigen-antibody reactions in order to detect antigens or antibodies in serum and other body fluids is particularly attractive when linked to flow cytometry. Flow cytometers have the capacity to detect particle size differences and are highly sensitive fluorescence detectors.

Microspheres can be sized by forward angle light scatter (FALS) or electronic volume. Used in conjunction with right angle light scatter (RALS), a flow cytometer (FCM) can distinguish between single and aggregated particles. By combining FALS and fluorescence, it is practical to use beads of several different sizes, each bead coated with a different proteins for the simultaneous detection of multiple analytes (antigens or antibodies). Microspheres can be coated with proteins passively or covalently depending on their chemical makeup.

The strengths of this type of assay are: 1) the ability to simultaneously, but discretely, analyze multiple analytes; 2) the simplicity of binding proteins to microspheres; 3) the ability of flow cytometry (FCM) to detect small particle size differences; and 4) the exquisite sensitivity of FCM as a detector of different wavelengths of fluorescence, simultaneously. Available auto-sampling systems make it even more appealing in this regard. The capacity to simultaneously detect multiple analytes in one tube in a immunoassay system suggests that immunoassays and biological probe assays may ultimately mimic multichannel chemistry analyzers with all of their benefits. Furthermore, the "no-wash" techniques, those procedures allowing the reagents to remain in the reaction container without centrifugation and supernatant decantation, greatly expedite the time in which results are available.

In accordance with one embodiment of the present invention, highly purified ScL-70, RNP, Sm, SS-A, SS-B and dsDNA antigens are bound to multiple sized latex beads, respectively and stabilized for extended shelf life. Diluted patient serum is placed into test tubes containing a mixture of five or six antigen coated beads and incubated. If an antibody is present for a specific antigen, it will bind to that specific bead. After washing (optional) the bead/serum mixture to remove residual sample, a second incubation with goat anti-human IgG, conjugated with a fluorochrome such as fluorescein isothiocyanate (FITC), is carried out. This conjugate will bind immunologically to the anti-antigen IgG of the antigen-antibody complex, forming a "sandwich" consisting of bead—antigen—1° antibody—2° antibody—FITC (FIG. 1).

Unbound conjugate is removed in the subsequent washing step. The fluorescence intensity is based on the avidity of the bead/antibody/conjugate binding The samples are analyzed using flow cytometers having laser excitation wavelengths of 488 nm. Emission wavelengths of 514 nm are detected by photomultipliers (PMTS) which convert the fluorescent analog signals into two parameter histograms expressing forward light scatter (Y-axis) versus fluorescence intensity (X-axis, FIG. 2).

In accordance with another embodiment of the invention, a fluorescent immuno-bead assay (FIBA) kit is used in conjunction with flow cytometry (FCM) for the simultaneous detection of the antinuclear antibodies to RNP (ribonucleo-protein) and dsDNA (double stranded DNA) seen in mixed connective tissue disease, systemic lupus erythematosus (SLE), Sjogren's syndrome, scleroderma and polymyositis; Sm (Smith antigen) in SLE; SS-A in Sjogren's syndrome and SLE; SS-B in Sjogren's syndrome and SLE; and Scl-70 in scleroderma. These antibodies are commonly encountered in the so-called rheumatic diseases.

By attaching each of these antigens to different sized latex beads, the presence of antibodies to one or more of these antigens can be rapidly detected and semi-quantitated. Instead of the five or more separate assays currently required, one assay involving five or more beads of different sizes in one tube provides the information needed. The cost saving in terms of materials, supplies, and technician time are estimated to be 60–70%. This can be further enhanced by utilizing robotic auto-sampling devices currently available or being developed for flow cytometry, for example, the Becton Dickinson Calibin with an auto-loader.

In accordance with another aspect of the present inventions, a platelet immunoglobulin (Ig) positive control reagent and assay are provided which utilize flow cytometry. Coated latex beads and labelled antibodies, to detect and quantify one or more analytes, and types of platelets (Type O) provide a positive control for each patient. Ig labeled beads may be added to platelet rich plasmas and utilized as a reagent control Normal platelets should not have Ig on their surface. In accordance with one embodiment of the present invention, immunoglobulin coating for IgG, IgM or IgA is bound to one or more latex beads, the same or different sizes, and stabilized for extended shelf life. In accordance with a direct platelet antibody procedure, an amount of Ig control material (beads) are added to respective tubes labelled IgG, IgM, IgA, and control. Thereafter, patient and control platelets are added to the respective tubes. Next, a specific goat Ig-FITC or goat anti-human Ig-FITC is added to the respective tubes. The tubes are then vortexed, incubated, washed, diluted and analyzed on a flow cytometer using forward scatter versus fluorescence (Fl1). Then, the positive region is determined by setting cursors on the control tube for that particular patient. Positivity is defined by all platelet intensities seen past the control region. In accordance with an indirect platelet antibody procedures type O platelets are used as a substrate for incubating with an amount of patient serum control or patient serum in respective tubes labelled Control, IgG, IgM, and IgA. After incubation the tubes are centrifuged, then the contents are decanted and gently vortexed. Next, a quantity of Ig control bead material is added to each tube labeled IgG, IgM, and IgA. Next, goat Ig-FITC, for the control tube, or goat anti-human Ig-FITC, for the other Ig, G, A & M tubes, is added. The tubes are then incubated, washed, resuspended, and read on a flow cytometer using forward scatter versus fluorescence (Fl1.) The positive region is then set based on the control tube for that patient.

A principal aspect of the present invention is the provision of an immunobead-flow cytometry assay for simultaneously detecting a plurality of antigens or antibodies in a sample.

A still further aspect of the present invention is the provision of a double wash fluorescent immunobead assay.

Yet another aspect of the present invention is the provision of a no-wash fluorescent immunobead assay.

Another more particular aspect of the present invention is a commercial assay kit designed to simultaneously detect several antibodies or antigens in patient sera utilizing antigen coated microspheres of different sizes. Binding of antibody to spheres is detected by FITC labelled anti-human IgG, A or M and flow cytometry. Each individual antibody is detected because of binding to a different sized sphere which is determined by light scatter.

Another aspect of the present invention is the provision of a platelet Ig positive control reagent.

Still another aspect of the present invention is the provision of a platelet Ig positive control assay.

Yet another aspect of the present invention is the provision of a improved Ig coating procedure.

A still further aspect of the present invention is the provision of a method and apparatus for detecting and quantifying viruses.

Another more particular aspect of the present invention is the provision of a method and apparatus for detecting and quantifying bacteria.

Future applications are essentially unlimited because the immunoassay of the present invention can be applied to any ligand binding system and the number of simultaneous assays can be expanded by the use of combinations of fluorophores and multiple microsphere sizes.

Other aspects and further scope of the applicability of the present invention will become apparent from the detailed description to follows taken in conjunction with the accompanying drawings wherein like parts are designated by like reference numerals.

DETAILED DESCRIPTION OF THE PREFERRED EMBODIMENTS

In accordance with an exemplary embodiment of the present invention, antigen coated latex surfaces, anti-nuclear antibodies, fluorescenated antibodies against such anti-nuclear antibodies, and flow cytometry are combined to provide multiparameter devices for the detection of a plurality of antigens in a single tube.

Figure 1:
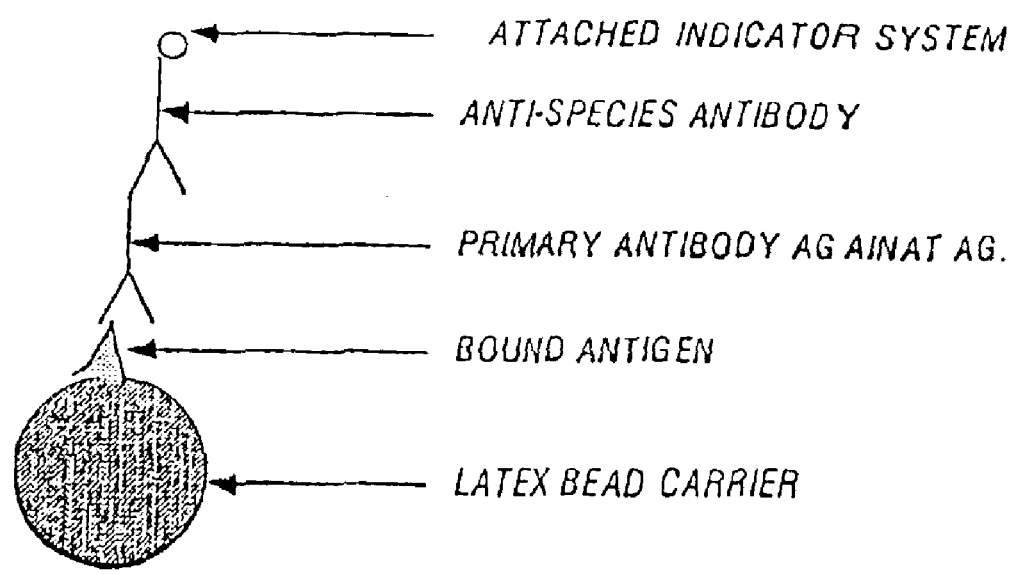
FIG. 1 is a schematic representation of an exemplary immunological structure of the bead-antigen-antibody indicator complex.

One basic principle of the present invention is to conjugate antigens or antibodies to the exterior of latex microspheres (beads) of different sizes. The coated microspheres are used to detect the appropriate specific antibodies or antigens simultaneously in one tube, with or without washing between sample incubation and indicator antibody phases. The ability to detect multiple analytes in one reaction tube eliminates the variability often seen in results arising from separate assays. Procedurally, latex beads are coated with specific antigens or antibodies. These beads vary in size and may also contain fluorescent dyes e.g. FITC, PE, etc. One or more of these precoated beads are then incubated with the sample (serum, body fluid) solution. If an antibody-antigen complex has been formed, a 2° indicator fluorochrome labelled antibody will bind to the appropriate bead (FIG. 1).

Figure 2:
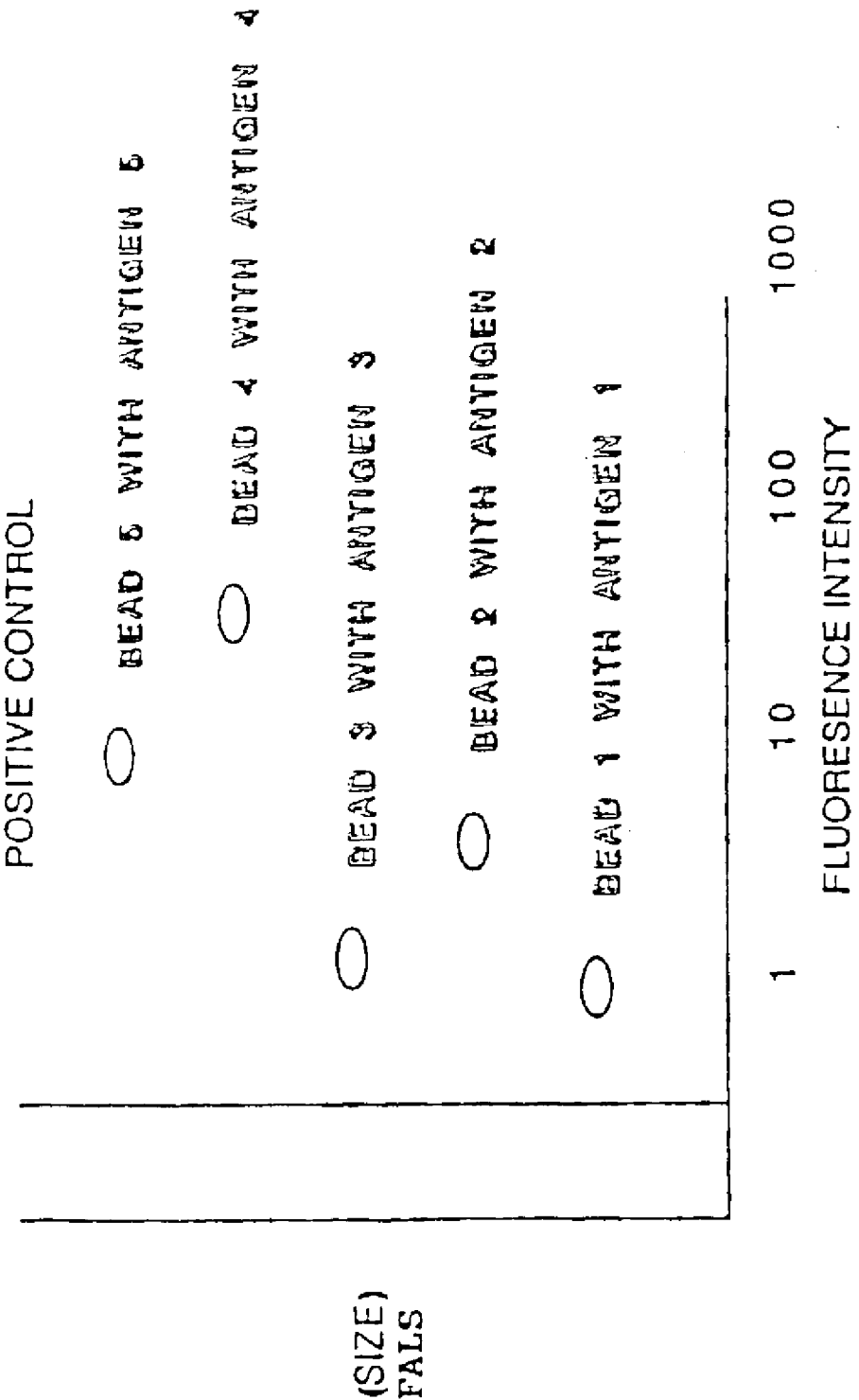
FIG. 2 is a schematic illustration of the flow cytometer histogram of forward angle light scatter (size) versus fluorescence on a positive control sample in a multiple bead system.
Figure 3:
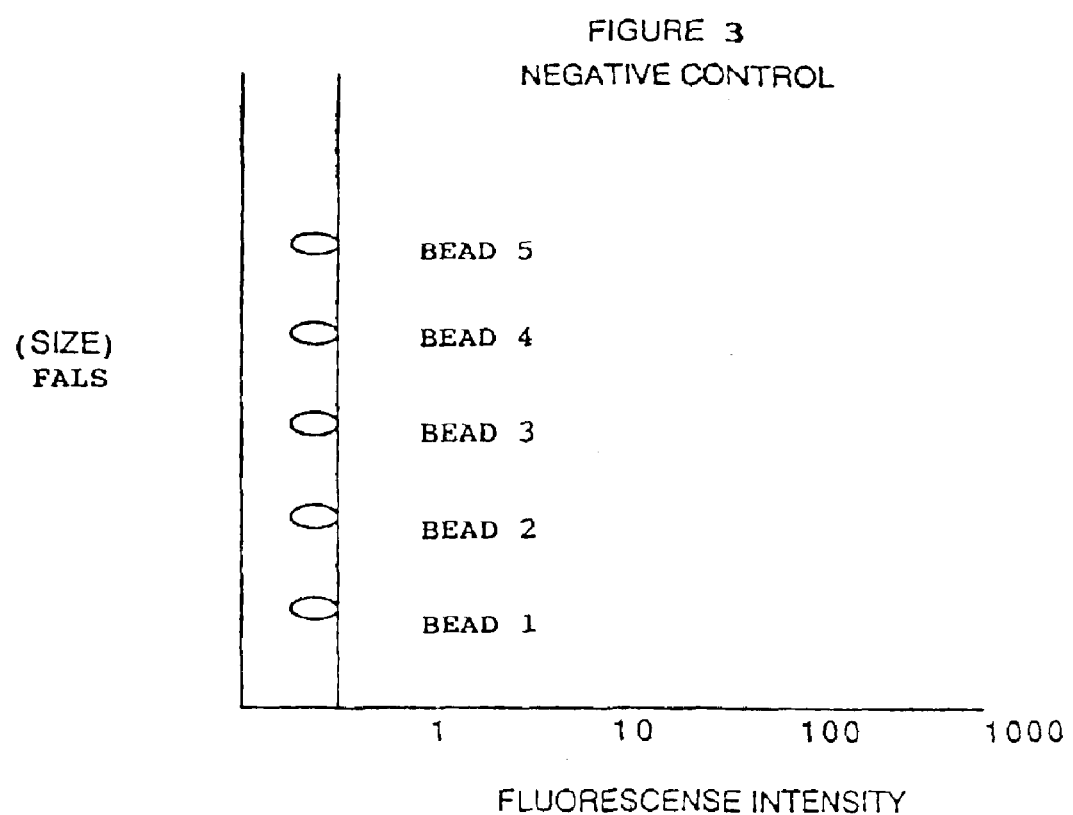
FIG. 3 is a schematic representation of a flow cytometer histogram of a negative control in a multiple bead system.

A no wash procedure is optional and has been utilized in most serum assays. However, as control substrates, washing may be necessary. The control beads are centrifuged, washed, and analyzed using forward angle light scatter to discriminate the different sized beads, each bound to a different antigen or antibody, and analyzed to detect fluorescence with a flow cytometer. The solution containing beads is passed through a series of tubes until it reaches the optical quartz cell of the flow cytometer. Because of the laminar flow of sheath fluid, single particle analysis is achieved. The signal is converted from analog to a digital display representing the size of the spheres and fluorescence of each (FIG. 2). Controls are used to adjust for the fluorescence background created by electronic and particle noise (FIG. 3). A forward scatter (size) adjustment of the multiple sized bead antigen or antibody complexes is necessary in order to semi-quantitate or quantitate the relative concentration of antigen or antibody on the bead surface through single screens visual distribution As seen in FIG. 3, a fluorescent threshold (x-axis) is established below which fluorescence values are considered negative. Upon addition of a "positive" sample, (containing appropriate antibody or antigen) the reaction between the fluorochrome labelled indicator antibody and antigen or antibody bead complex, amplifies the fluorescence signals detected by the flow cytometer (FIG. 2). Thus, the definition of "positivity" in this system is relative to the negative control (background) and can easily be interpreted.

Figure 4:
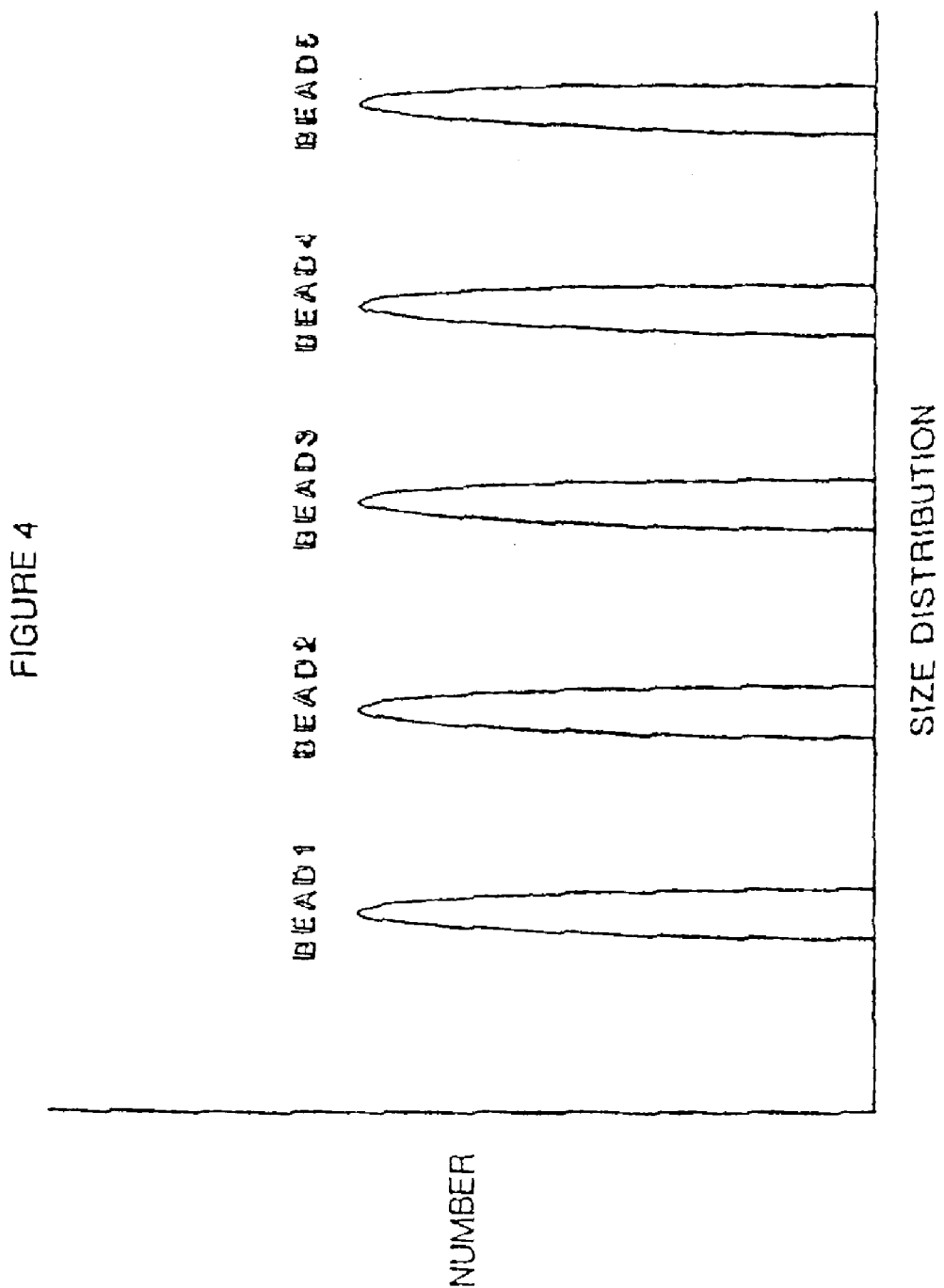
FIG. 4 is a schematic illustration of a flow cytometer histogram of the size characteristics of latex beads when run on a flow cytometer.

Multiple antibodies or antigens can readily be displayed and quantitative values obtained in a single two-dimensional histogram. Similarly, additional bead systems can be combined within the size distinguishing capabilities of the flow cytometer and the sizes available from vendors providing latex particles (FIG. 4). As seen in FIG. 1, the multiple antigen or antibody coated bead system incorporates specific anti-species specific 2° antibodies, labelled with fluorochromes (e.g., FITC, PE) to detect the presence of antigen-antibody complexes on the beads. All other antibodies non-specifically bound to the latex surface are either washed away or ignored by the indicator antibody.

The present invention uses the principles of flow cytometry and light scatter to detect different sizes of latex particles with fluorescence as the endpoint. Distinction from celluluar material is also accomplished through these procedures. Multiple antigens or antibodies in body fluids are detected simultaneously in a single tube because each specific antibody or antigen is differentiated by the size of the bead it is bound to. This invention differs from the procedure disclosed in U.S. Pat. No. 5,162,863 in that the latter measures the presence of the amount of a plurality of kinds of particular antigens or antibodies in a specimen at a time by a simple construction without the use of fluorescence.

Advantages of the present invention include:
1. Because of varying sizes and dyes of microspheres, multiple antibodies or antigens can be detected and quantitated simultaneously in a single tube.
2. Specific antibodies/antigens can much more easily be detected when bound to latex bead surfaces due to the separation of one antigen/antibody from the other.
3. Because of the sensitivity of fluorescence based flow cytometry this assay tends to be capable of detecting lower levels of antibodies/antigens than other conventional assay methods e.g. EIA, ELISA, agglutination etc.
4. Because of a relatively unlimited range of bead sizes, other bead physical characteristics, fluorochromes and probes this invention offers great flexibility.
5. Single tube analysis, wash or no-wash, facilitates the utilization of "batch-mode" processing and automation.
6. The present assay system can be used in screening, semi-quantitative or quantitative methods.
7. Almost any flow cytometer may be utilized for this method.
8. Minimal volumes of sample are necessary in order to run multiple assays.
9. Materials bound to the latex bead surface may be antigens, antibodies, chemicals, microorganisms, cell components, and other substances capable of binding specifically to an appropriate ligand, including DNA and RNA for in situ hybridization.

EXAMPLE 1

Double Wash Detection System

In accordance with one example of the present invention, five distinct latex beads coated with a unique antigen are incubated with diluted human serum and then labelled with goat anti-human FITC labelled antibodies. Positivity is distinguished or semi-quantitated using a blank or isotopic control as the negative standard. Forward scatter (forward angle light scatter, FALS, size) versus green fluorescence are used to detect positivity.

Purified antigens, positive control sera, human antibodies, monospecific donor plasma, anti-human antibodies, etc. for autoimmune testing are commercially available. For example, other affinity purified, highly immunospecific, antigens such as Ro(SS-A), La(SS-B), Sm(Smith), Sm/RNP, Scl-70, Jo-1 and dsDNA as well as purified whole histones and histone subclasses (distinct molecular fractions) are available. Positive control sera for autoimmune testing, human antibodies against Ro(SS-A), La(SS-B), Sm, RNP, Scl-70, Jo-1, PM-1, monospecific donor plasma against Cardiolipin, dsDNA, Jo-1, Mitochondrial, PCNA, PM-1, Po, RNP, Scl-70, Sm, Ro(SS-A), La(SS-B), and thyroid microsomal, animal tissue acetone powders, animal sera and immunoglobulin fractions (whole serum, gamma fractions, purified IgG), animal second antibodies (whole antisera, IgG fractions, affinity purified) anti-whole sera, mouse antisera, and whole antisera to selected animal and human proteins are commercially available.

Materials

4 $\mu$m particle sized latex bead, Duke Scientific, Cat #4204A
5 $\mu$m particle sized latex beads Duke Scientific, Cat #4205A
6 $\mu$m particle sized latex bead, Duke Scientific, Cat #4206A
7 $\mu$m particle sized latex beads Duke Scientific, Cat #4207A
3 $\mu$m particle sized latex beads Duke Scientific, Cat #4203A
Sm/RNP Complex antigen, Immunovision, Cat #SCR-3000
Sm antigen, 1000 units, Immunovision, Cat #SMA-3000
SS-A (Ro) antigen, 1000 units, Immunovision, Cat #SSA-3000
SS-B (La) antigen, 1000 units, Immunovision, Cat #SSB-3000 Scl-70
antigen, 1000 units, Immunovision, Cat #SCL-3000
Anti-RNP, lyophilyzed, Immunovision, Cat #HRN-0100
Anti-Sm, lyophilyzed, Immunovision, Cat #HSM-0100
Anti-SS-A (Ro) lyophilyzed, Immunovision, Cat #HSA-0100

Anti-SSB (La) lyophilyzed, Immunovision, Cat #HSC-0100
Anti-Scl-70, lyophilyzed, Immunovision, Cat #HSC-0100
Goat anti-human IgG F(ab')$_2$-FITC, Tago, Inc., Cat #4200
Sodium Carbonate, Sigma Chemical, Cat #S-6139
Sodium Bicarbonate, Baker Chemical, Cat #3506-1
Albumin, bovine, Sigma Chemical, Cat #A-7888
200 µl adjustable pipettor
pipettor tips
10 mL pipettes
Centrifuge
12×75 mL polystyrene test tubes
13 mm caps
flow cytometer
Reagents
Carbonate Buffer, pH 9.6
1. Add 1.5 g of sodium carbonate and 0.8 g of sodium bicarbonate to 500 mL of distilled water.
2. Mix for 5–10 minutes or until all crystals are dissolved.
3. Adjust pH to 9.6 using 2N NaOH.
4. A Store at 4–8° C.
5. Buffer only to be used for less than 48 hours after preparation. For antigen coating only.
0.5% Albumin, Bovine in PBS
   1. Mix 0.5 g of bovine albumin in 100 mL of PBS.
   2. Mix thoroughly.
   3. Store at 4–8° C. for one month.
Procedure
1. Determine the amount of latex bead suspension (e.g. # of drop w/mL carbonate buffer) needed to achieve an event count of 900–1000 beads/second on the flow cytometer.
2. Titer antigen (Ag) to appropriate µg/mL and use concentration deemed optimal for maximum mean channel and fluorescence.
3. Add antigen to each respective tube: (µg)

| Antigen (size bead) | Drops/mL Buffer | Ag/mL Buffer |
| --- | --- | --- |
| Scl-70 (3 µm) | 3 | 10 |
| RNP (4 µm) | 3 | 30 |
| Sm (5 µm) | 3 | 10 |
| SS-A (6 µm) | 6 | 15 |
| SS-B (7 µm) | 6 | 15 |

4. Incubate bead/antigen mixture for 12–18 hours at 4–8° C.
5. Centrifuge solution at full speed in a refrigerated centrifuge for 10 minutes.
6. Decant supernatant and gently resuspend beads by hand.
7. Add 1 mL of 0.5% albumin in PBS per mL original volume.
8. Gently vortex.
9. Repeat steps 5 and 6.
10. Add 1 mL of carbonate buffer per original milliliters of antigen/bead solution.
11. Add 100 uL of each antigen/bead mixture to all reaction tubes.
12. Dilute positives negative and patient serum 1:100 in protein buffer.
13. Add 15 µL of each serum diluted to appropriately labelled tube.
14. Vortex gently and incubate for 15 minutes at room temperature.
15. Wash once with 1 mL carbonate buffer.
16. Repeat steps 5 and 6.
17. Add 50 µL of Goat anti-human IgG F(ab')$_2$-FITC 1.20 (NOTE: dilution may slightly vary from lot to lot. Titer all new lots).
18. Gently vortex and incubate 15 minutes at room temperature.
19. Repeat steps 5 and 6.
20. Add 0.5 mL of carbonate buffer.
21. Read on flow cytometer.

EXAMPLE 2

Double Wash Detection System

In accordance with another example of the present inventions an immunobead-flow cytometry method for simultaneously detecting a plurality of antigens is as follows.
Procedure
1. Determine the amount of latex bead suspension (e.g. # of drop w/mL carbonate buffer) needed to achieve an event count of at least 500 beads/second on the flow cytometers.
2. Titer antigen (Ag) to appropriate µg/mL and use concentration deemed optimal for maximum mean channel and fluorescence.
3. Add antigen to each respective tube. (µg)

| Antigen (size bead) | Drops/mL Buffer | Ag/mL Buffer |
| --- | --- | --- |
| RNP (0.25 µm) | 3 | 30 |
| Sm (0.50 µm) | 3 | 10 |
| SS-A (0.75 µm) | 6 | 15 |
| SS-B (1.0 µm) | 6 | 15 |
| Scl-70 (1.25 µm) | 10 | 10 |

4. Incubate bead/antigen mixture for 12–18 hours at 4–8° C.
5. Centrifuge solution at full speed in a refrigerated centrifuge for 10 minutes.
6. Decant supernatant and gently resuspend beads by hand.
7. Add 1 mL of 0.5% albumin in PBS per mL original volume.
8. Gently vortex.
9. Repeat steps 5 and 6.
10. Add 1 mL of carbonate buffer per original milliliters of antigen/bead solution.
11. Add 100 uL of each antigen/bead mixture to all reaction tubes or add a pre-mixed amount of 500 µL of the 5 antigen-coated bead suspension.
12. Add 15 µL of a 1:100 dilution of patient or control serum diluted in protein buffer.
13. Gently vortex and incubate for 15 minutes at room temperature.
14. Make at least 1:5 dilution of Goat anti-human F (ab')$_2$ IgG-FITC in 0.5% albumin solution in PBS.
15. Add 50 µL of diluted conjugate to the bead suspension.
16. Incubate for 15 minutes at room temperature in the dark.
17. Add 1 mL of PBS.
18. Analyze on flow cytometer.

Cytometer adjustments of fluorescent gains will change, therefore, it is recommended that a blank and normal control be run as reference material. Conjugate titers may vary, serial dilutions must be made on all new lots.

EXAMPLE 3

Double Wash Detection System

In accordance with yet another example of the assay of the present invention the method follows.
Procedure
1. Determine the amount of latex bead suspension (e.g. # of drop w/mL carbonate buffer) needed to achieve an event count of 900–1000 beads/second on the flow cytometer.

2. Titer antigen (Ag) to appropriate μg/mL and use concentration deemed optimal for maximum mean channel and fluorescence.
3. Add antigen to each respective tube: (μg)

| Antigen (size bead) | Drops/mL Buffer | Ag/mL Buffer |
|---|---|---|
| RNP (660 μm) | 3 | 30 |
| Sm (680 μm) | 3 | 10 |
| SS-A (700 μm) | 6 | 15 |
| SS-B (720 μm) | 6 | 15 |
| Scl-70 (740 μm) | 10 | 10 |

4. Incubate bead/antigen mixture for 12–18 hours at 4–8° C.
5. Centrifuge solution at full speed in a refrigerated centrifuge for 10 minutes.
6. Decant supernatant and gently resuspend beads by hand.
7. Add 1 mL of 0.5% albumin in PBS per mL original volume.
8. Gently vortex.
9. Repeat steps 5 and 6.
10. Add 1 mL of carbonate buffer per original milliliters of antigen/bead solution.
11. Add 100 uL of each antigen/bead mixture to all reaction tubes.
12. Dilute positives negative and patient serum 1:100 in protein buffer.
13. Add 15 μL of each serum diluted to appropriately labelled tube.
14. Vortex gently and incubate for 15 minutes at room temperature.
15. Wash once with 1 mL carbonate buffer.
16. Repeat steps 5 and 6.
17. Add 50 μL of Goat anti-human IgG F(ab')$_2$-FITC 1:20 (NOTE: dilution may slightly vary from lot to lot. Titer all new lots).
18. Gently vortex and incubate 15 minutes at room temperature.
19. Repeat steps 5 and 6.
20. Add 0.5 mL of carbonate buffer.
21. Read on flow cytometer.

EXAMPLE 4
Double Wash Detection System

In accordance with still another example of the present invention the assay is as follows.
Procedure
1. Determine the amount of latex bead suspension (e.g. # of drop w/mL carbonate buffer) needed to achieve an event count of 900–1000 beads/second on the flow cytometer.
2. Titer antigen (Ag) to appropriate μg/mL and use concentration deemed optimal for maximum mean channel and fluorescence.
3. Add antigen to each respective tube: (μg)

| Antigen (size bead) | Drops/mL Buffer | Ag/mL Buffer |
|---|---|---|
| Scl-70 (#μm) | 3 | 10 |
| Sm/RNP (4 μm) | 3 | 30 |
| SM (5 μm) | 3 | 10 |
| Ro/SS-A (6 μm) | 6 | 15 |
| La/SS-B (7 μm) | 6 | 15 |
| dsDNA (8 μm) | 10 | 10 |

4. Incubate bead/antigen mixture for 12–18 hours at 4–8° C.
5. Centrifuge solution at full speed in a refrigerated centrifuge for 10 minutes.
6. Decant supernatant and gently resuspend beads by hand.
7. Add 1 mL of 0.5% albumin in PBS per mL original volume.
8. Gently vortex.
9. Repeat steps 5 and 6.
10. Add 1 mL of carbonate buffer per original milliliters of antigen/bead solution.
11. Add 100 uL of each antigen/bead mixture to all reaction tubes.
12. Dilute positives negative and patient serum 1:100 in protein buffer.
13. Add 50 μL of each serum diluted to appropriately labelled tube.
14. Vortex gently and incubate for 15 minutes at room temperature.
15. Wash once with 1 mL carbonate buffer.
16. Repeat steps 5 and 6.
17. Add 50 μL of Goat anti-human IgG F(ab')$_2$-FITC 1:20 (NOTE: dilution may slightly vary from lot to lot. Titer all new lots).
18. Gently vortex and incubate 15 minutes at room temperature.
19. Repeat steps 5 and 6.
20. Add 0.5 mL of carbonate buffer.
21. Read on flow cytometer.

EXAMPLE 5
Double Wash Detection System

In accordance with another example of the present invention the multiple parameter bead assay is as follows.
Procedure
1. Determine the amount of latex bead suspension (e.g. # of drop w/mL carbonate buffer) needed to achieve an event count of 900–1000 beads/second on the flow cytometer.
2. Titer antigen (Ag) to appropriate μg/mL and use concentration deemed optimal for maximum mean channel and fluorescence.
3. Add antigen to each respective tube: (μg)

| Antigen (size bead) | Drops/mL Buffer | Ag/mL Buffer |
|---|---|---|
| dsDNA (4 μm) | 3 | 30 |
| Ribosomal P (5 μm) | 3 | 10 |
| Mitochondria (6 μm) | 6 | 15 |
| Histone H1 (7 μm) | 6 | 15 |
| Centromere (8 μm) | 8 | 10 |
| Histone H2A (10 μm) | 10 | 10 |

4. Incubate bead/antigen mixture for 12–18 hours at 4–8° C.
5. Centrifuge solution at full speed in a refrigerated centrifuge for 10 minutes.
6. Decant supernatant and gently resuspend beads by hand.
7. Add 1 mL of 0.5% albumin in PBS per mL original volume.
8. Gently vortex.
9. Repeat steps 5 and 6.
10. Add 1 mL of carbonate buffer per original milliliters of antigen/bead solution.
11. Add 100 uL of each antigen/bead mixture to all reaction tubes.
12. Dilute positive, negative and patient serum 1:100 in protein buffer.
13. Add 15 μL of each serum diluted to appropriately labelled tube.
14. Vortex gently and incubate for 15 minutes at room temperature.
15. Wash once with 1 mL carbonate buffer.

16. Repeat steps 5 and 6.
17. Add 50 μL of Goat anti-human IgG F (ab')$_2$-FITC 1:20 (NOTE: dilution may slightly vary from lot to lot. Titer all new lots).
18. Gently vortex and incubate 15 minutes at room temperature.
19. Repeat steps 5 and 6.
20. Add 0.5 mL of carbonate buffer.
21. Read on flow cytometer.

In parallel examples, all of the above examples are carried out without steps involving washing reaction mixtures.

Figure 5:
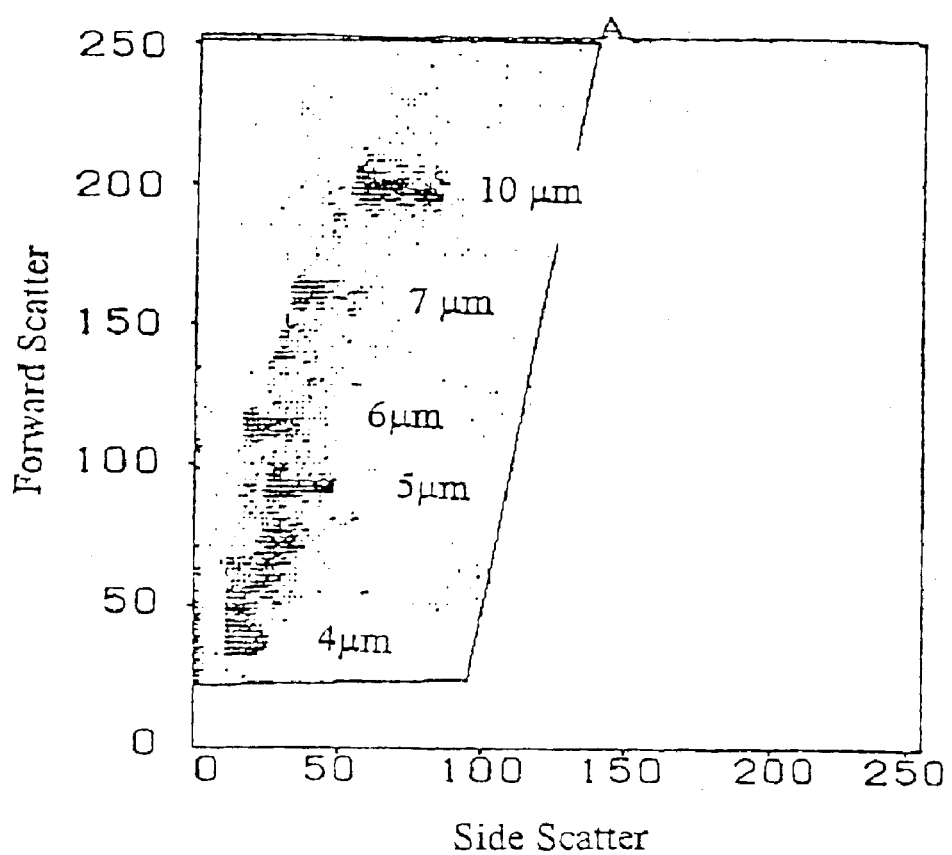
FIG. 5 is a representation of a flow cytometer cytogram of the size and complexity distribution as is seen with a patient sample of beads coated with antigen and analyzed in a flow cytometer.
Figure 6:
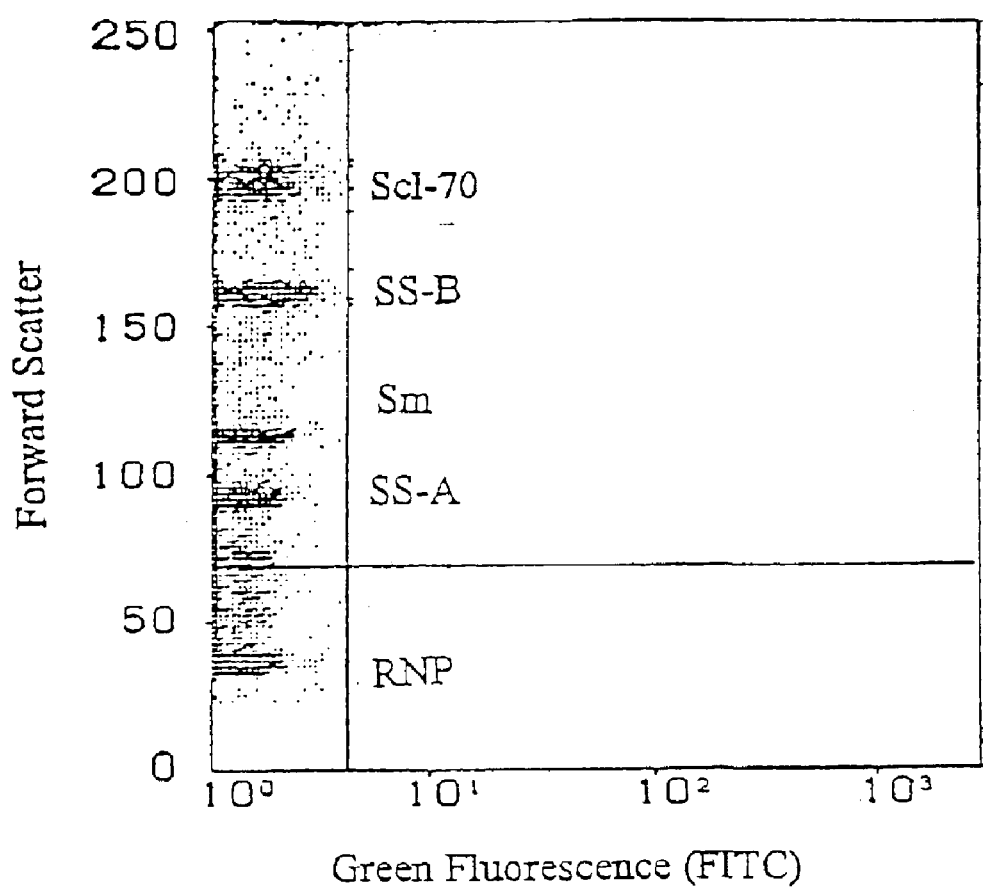
FIG. 6 is an illustration of a flow cytometer histogram of coated beads incubated with a negative control sample.
Figure 7:
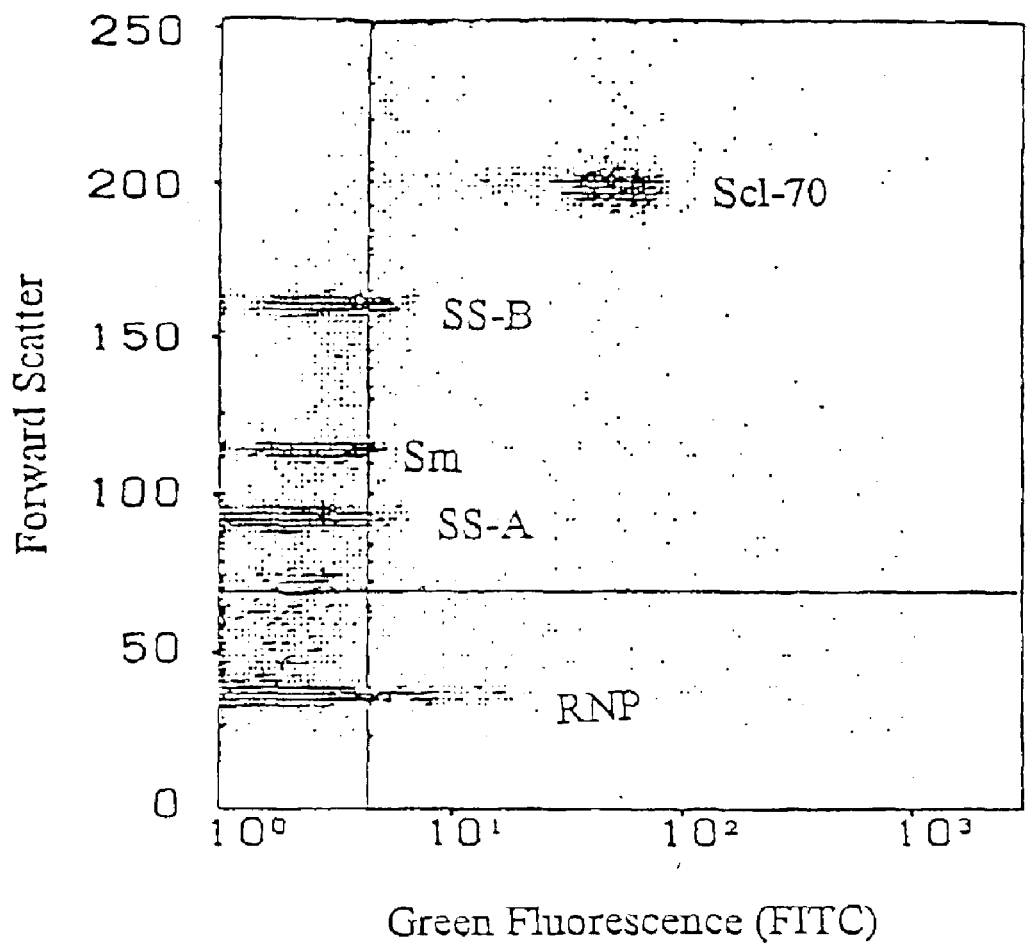
FIG. 7 is a representation of a flow cytometer histogram of a positive sample in which antibody to Scl-70 is present, but no antibodies to the other antigens are present.

It has been demonstrated that multiple antigens can be attached to latex beads of the following sizes, 4, 5, 6, 7, and 10 μm; respectively (FIG. 5). After incubation with sera from patients with antibodies to these antigens, followed by the addition of fluorescenated anti-human IgG, beads that have bound antibody fluoresce and are specifically detectable because of their size differences (FIGS. 1, 2, 6, & 7). However, other antigens may be attached in a similar fashion and with or without washing the reaction tube. Other sized beads may be added or subtracted.

The results of the assays of the present invention are improved by determining 1) optimal concentrations of antigens on latex microspheres using block titration methods; 2) optimal ratios of serum to bead concentrations; and 3) optimal concentrations of secondary antibody (anti-human IgG). Once optimal antigen-bead-antibody concentrations are determined and, using commercially available human sera containing these anti-bodies, antigen coated beads are incubated with various dilutions of sera and secondary (detector) antibody. Several dilutions of known positive sera are performed to determine the sensitivity of the assay.

Figure 8:
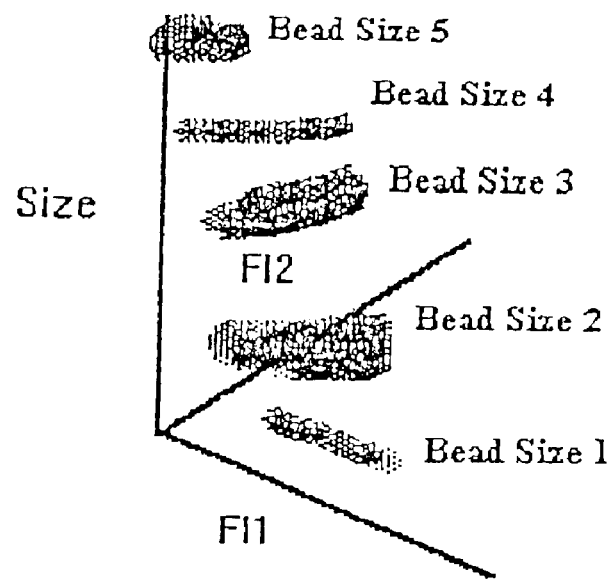
FIG. 8 is an illustration of a three dimensional flow cytometer histogram of the three parameters of bead size, first fluorescence color (Fl1), and second fluorescence color (Fl2)
Figure 9:
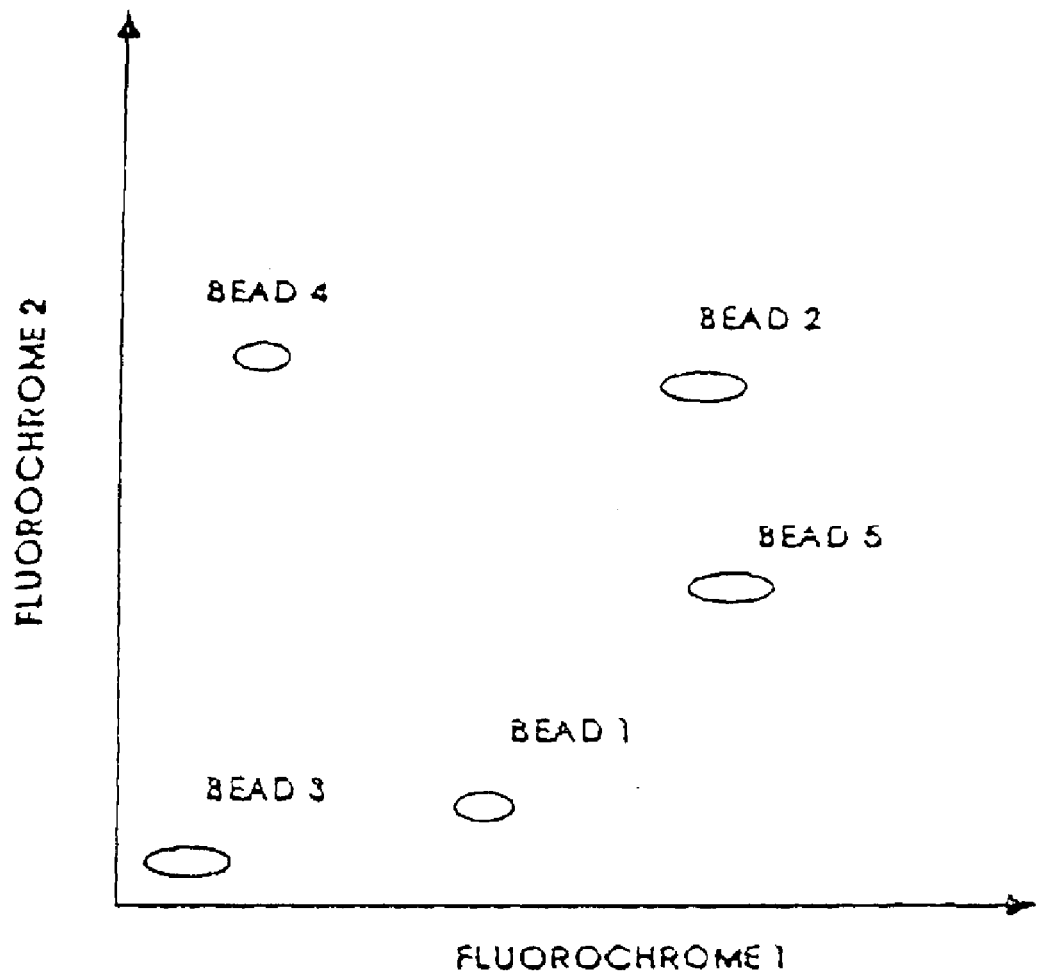
FIG. 9 is a schematic representation of a two dimensional flow cytometer histogram of different sized beads labelled with different fluorochromes.

The methodology of the present invention provides that microsphere sizes are combined with two color FCM and results displayed three dimensionally as a "cloud" display (FIG. 8). This increases the number of antibodies or antigens to be simultaneously analyzed (FIG. 9).

EXAMPLE 6
Multiple Parameter Detection System

In accordance with another embodiment of the present invention, highly purified Scl-70, RNP, Sm, SS-A, SS-B and dsDNA antigens are bound to 3, 4, 5, 6, 7 and 8 μm latex beads, respectively and stabilized for extended shelf life. Diluted patient serum is placed into test tubes containing a mixture of the six antigen coated beads and incubated. If an antibody is present for a specific antigen, it will bind to that specific bead. After washing (optional) the bead/serum mixture to remove residual sample, a second incubation with goat anti-human IgG, conjugated with fluorescein isothiocyanate (FITC), is carried out. This conjugate will bind immunologically to the anti-antigen IgG of the antigen-antibody complex, forming a "sandwich" consisting of bead—antigen—1° antibody—2° antibody—FITC (FIG. 1).

Unbound conjugate is removed in the subsequent washing step (optional). The fluorescence intensity is based on the avidity of the bead/antibody/conjugate binding The samples are analyzed using flow cytometers having laser excitation wavelengths of 488 nm. Emission wavelengths of 514 nm are detected by photomultipliers which convert the fluorescent analog signals into two parameter histograms expressing forward light scatter (Y-axis) versus fluorescence intensity (X-axis, FIG. 2).

In accordance with another embodiment of the present invention, a "no wash" immunoassay, immunobead-flow cytometry highly purified Scl-70, RNP, Sm, SS-A, SS-B, and/or dsDNA antigens are bound to 3, 4, 5, 6, 7 and 8 μm latex beads, respectively and stabilized for extended shelf life. Diluted patient serum is placed into test tubes containing a mixture of six antigen coated beads and incubated. If an antibody is present for a specific antigen, it will bind to that specific bead. Next, a dilution of goat anti-human IgG-FITC in albumin in PBS is added and a second incubation is carried out. This conjugate will bind immunologically to the anti-antigen IgG of the antigen-antibody complex, forming a "sandwich" consisting of bead—antigen—1° antibody—2° antibody—FITC (FIG. 1). Then, the samples are analyzed on a flow cytometer.

EXAMPLE 7
One Step Bead Detection System
No Wash Detection System

The following "no wash" procedure is a modification of the above bead evaluation method and utilizes an albumin step in the conjugate to eliminate non-specific staining resulting from increased patient serum protein concentrations.

1. Allow reagents to come to room temperature.
2. Gently invert antigen coated bead mixture until an even distribution of bead product is observed.
3. Label test tubes for Controls and Patients.
4. Add 500 μL of pre-mixed bead suspension to each tubes or 600 uL if dsDNA is part of the assay.
5. Dilute patient and control serum 1:100 in protein buffer (e.g. 5 μL serum to 495 μL saline).
6. Add 15 μL of diluted serum to appropriate test tubes.
7. Gently vortex and incubate for 15–30 minutes at room temperature.
8. Make at least a 1:5 dilution of goat anti-human F (ab')$_2$ IgG FITC (or other fluorochrome) in PBS.
9. Add 50 μL of diluted conjugate to each tube.
10. Gently vortex and incubate for 15–30 minutes at room temperatures, in the dark.
11. Analyze on flow cytometer.

EXAMPLE 8
No Wash Detection System

1. Allow reagents to come to room temperature.
2. Gently invert antigen coated bead mixture until an even distribution of bead product is observed.
3. Label test tubes for Blank, Controls, and Patients.
4. Add at least 100 μL of bead suspension to each tube.
5. Dilute patient and control serum at least 1:100 in saline (e.g. 10 μL serum to 990 μL saline).
6. Add at least 15 μL of diluted serum to appropriate test tubes.
7. Add at least 10 μL of PBS to blank tube.
8. Gently vortex and incubate for at least 5 minutes at room temperature.
9. Make an at least 1:2 dilution of labelled anti-human antibodies in at least 0.2% albumin in PBS.
10. Add at least 10 μL of diluted conjugate to each tube.
11. Gently vortex and incubate for at least 5 minutes at room temperatures, in the dark.
12. Add about 1 mL of PBS to each tube.
13. Analyze on flow cytometer.

EXAMPLE 9
No Wash Detection System

1. Allow reagents to come to room temperature.
2. Gently invert antigen coated bead mixture until an even distribution of bead product is observed.
3. Label test tubes for Blank, Controls, and Patients.
4. Add equal quantities of bead suspension to each tube.
5. Dilute patient and control serum to about 1:20 in saline (e.g. 10 μL serum to 190 μL saline).

6. Add equal quantities of diluted serum to appropriate test tubes.
7. Add the same quantity of PBS to blank tube.
8. Gently vortex and incubate at room temperature.
9. Make an about 1:5 dilution of labelled anti-human antibody in about 0.5% albumin in PBS.
10. Add equal quantities of diluted conjugate to each tube.
11. Gently vortex and incubate at room temperature.
12. Add equal quantities of PBS to each tube.
13. Analyze on flow cytometer.

EXAMPLE 10

No-Wash Anti-ENA Screening Assay Test Kit

In accordance with still another embodiment of the present invention, an FIBA-FCM assay test kit is described as follows.

Summary of Procedure

1. Add 15 µL of sample to 600 µL of RNP, Sm, SS-A(Ro), SS-B(La), Scl-70 and dsDNA coated bead solution Mix well.
2. Incubate at room temperature for 15 minutes.
3. Place one drop (approximately 50 uL) of fluorescenated conjugate into each tube. Mix well.
4. Incubate at room temperatures in the dark, for 15–30 minutes.
5. Read on flow cytometer.

Intended Use of Kit

For the simultaneous detection of anti-antibodies to the antigens RNP, Sm, SS-A(Ro) SS-B(La) Scl-70 and dsDNA in serum as an aid in the diagnosis and of certain so-called rheumatic or connective tissue diseases, e.g. systemic lupus erythematosus (SLE) Sjogren's syndrome, scleroderma, and polymyositis. For in vitro Diagnostic Use. Other antigens associated with different conditions may be added. Analysis of beads may be as individual beads or combined to make different hits.

Summary and Explanation

Current approaches to the detection of auto-antibodies in these diseases are through the use of ELISA or immunodiffusion assays. The above flow cytometry method shortens turnaround times, decreases technical manipulations, increases sensitivity, eliminates the use of multiple plates, and decreases laboratory costs.

The above assay is a flow cytometric based procedure intended for the no-wash, semi-quantitation of antibodies to RNP, Sm, SS-A(Ro), SS-B(La), dsDNA and Scl-70. The results are reported in a semi-quantitative fashion using linear fluorescence scales derived from the flow cytometers themselves. Gradations are strictly standardized against negative and positive controls.

Principle and Procedure

Highly purified Scl-70, RNP, Sm, SS-A, SS-B, and dsDNA antigen are bound to respective 3, 4, 5, 6, 7 and 8 µm latex beads and stabilized for extended shelf life. Diluted patient's sera are placed into test tubes containing a mixture of the six antigen coated beads and incubated. If an antibody is present to the specific antigen (i.e. bead), it will bind to that specific bead. A second incubation with goat anti-human IgG conjugated with fluorescein isothiocyanate (FITC) is carried out. Conjugate will bind immunologically to the anti-antigen IgG of the antigen-antibody complex, forming a "sandwich" (FIG. 1).

The fluorescence intensity is based on the avidity of the bead/antibody/conjugate binding. The samples are analyzed using flow cytometers having laser excitation wavelengths of 488 nm. Emission wavelengths of 514 nm are detected by photomultipliers which convert the fluorescent analog signals into digital signals two parameter histograms (size (Y-axis) versus fluorescent intensity (X-axis, FIG. 2).

Detailed Procedure

Allow test components and patient samples to warm to room temperature before use. Return promptly to refrigerator after use.

1. Properly label sufficient numbers of test tubes to identify positive and negative controls and patient samples.
2. Add 600 µL of a solution containing each bead suspension into each of the labelled test tubes.
3. Prepare 1:20 dilutions of the Positive and Negative Controls, (Unless prediluted in kit) and the patient samples, by adding 10 µL of each to 990 µL of sample diluent (in test tubes or microtiter plate provided).
4. Mix sample dilutions gently by withdrawing and expelling in a pipette tip 2 or 3 times (microtiter plate) or vortexing.
5. Transfer 15 µL of each diluted control or patient sample into corresponding test tube.
6. Gently vortex and incubate at room temperature (20 to 30° C.) for 15–30 minutes.
7. Add one drop (approximately 50 µL) of diluted fluorescenated conjugate to each tube.
8. Gently vortex and incubate for 15–30 minutes at room temperature in the dark.
9. Analyze on flow cytometer.

NOTE. Analysis should be made within 2 hours of final staining.

Calculation of Results

The evaluation of specimens is based on a semi-quantitation of the fluorescent intensity Calculations are directly related to the linear scale used on the FL1 x-axis. Samples will therefore be gated by two-parameter settings (e.g. forward angle light scatter and FL 1). Adjust the FL1 PMT of the normal control to where the smallest size bead has approximately a mean channel of 20. This will determine the degree of positivity (FIG. 2) of the other control and patient samples Scl-70, RNP, Sm, SS-A, SS-B, and dsDNA must be read by using the schematic below.

For semi-quantitive results, divide the mean channel fluorescence at the normal (negative) control into the means channel of the positive control or patient samples. This will give the operator a normalized index Cut-off ranges for positivity may be different for each antigen/bead combination.

Patient samples which contain positive antibody will give fluorescent index results greater than 1.5 units. If an accurate semi-quantitative end-point titer unit is necessary, make serial dilutions of the patient sample, reassay, and report the index while indicating the final dilution factor that generates a positive result.

Calibration

The assay reagents should be adjusted for optimal concentrations for the flow cytometers mentioned before. The positive control must fall within the ranges established for that lot. Slight variations in intensity may arise depending on a labs preference for gain and detector settings.

Figure 10:
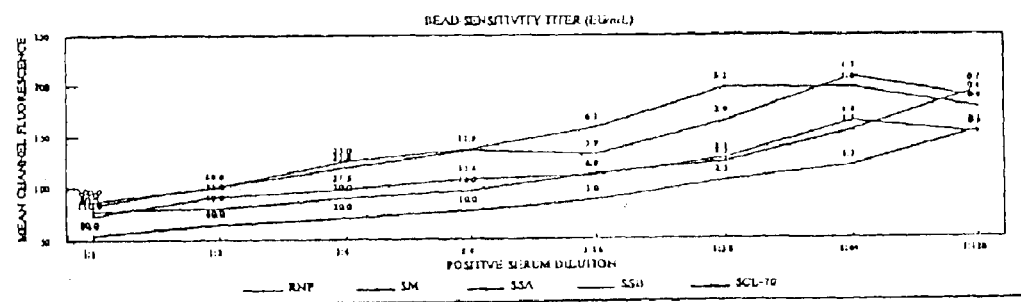
FIG. 10 is a tabular and graphical representation of flow cytometer assay sensitivity results of fluorescence versus positive serum dilution.
Figure 11:
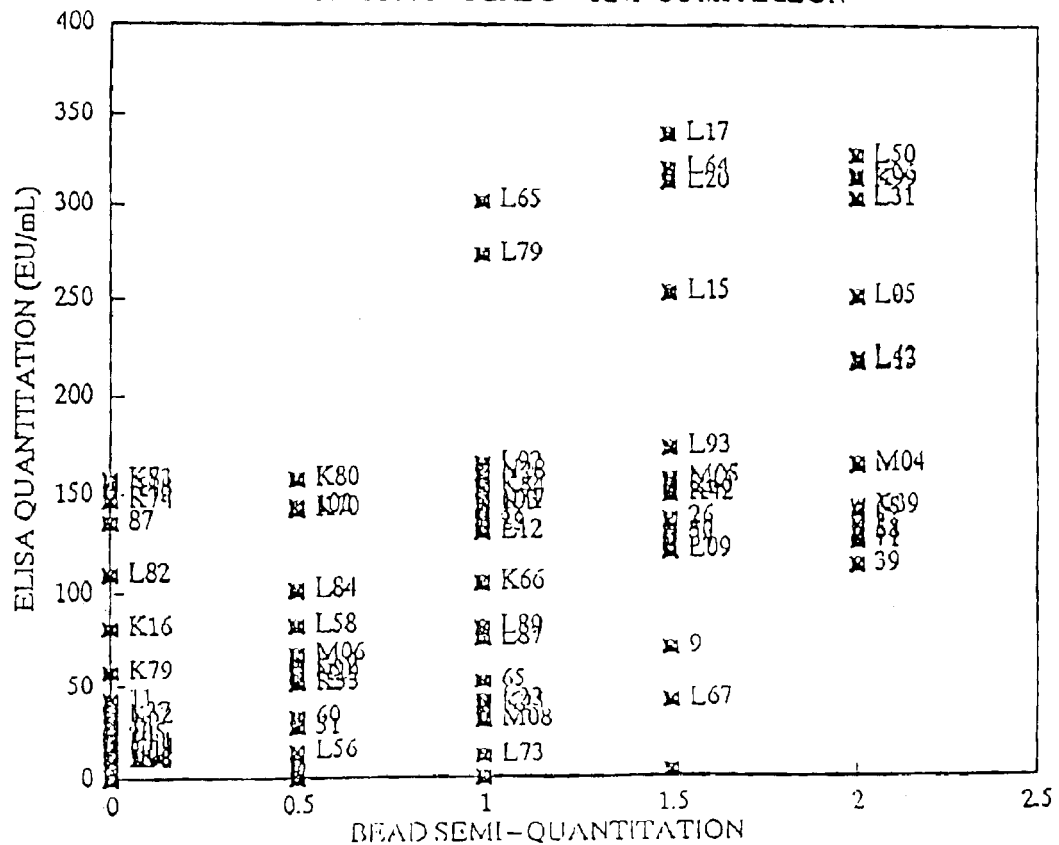
FIGS. 11–15 are graphical illustrations of comparative quantitation results of ELISA assay versus the double wash bead assay of the present invention relating to the respective antigens RNP, Sm, SS-A, SS-B, and Scl-70.
Figure 12:
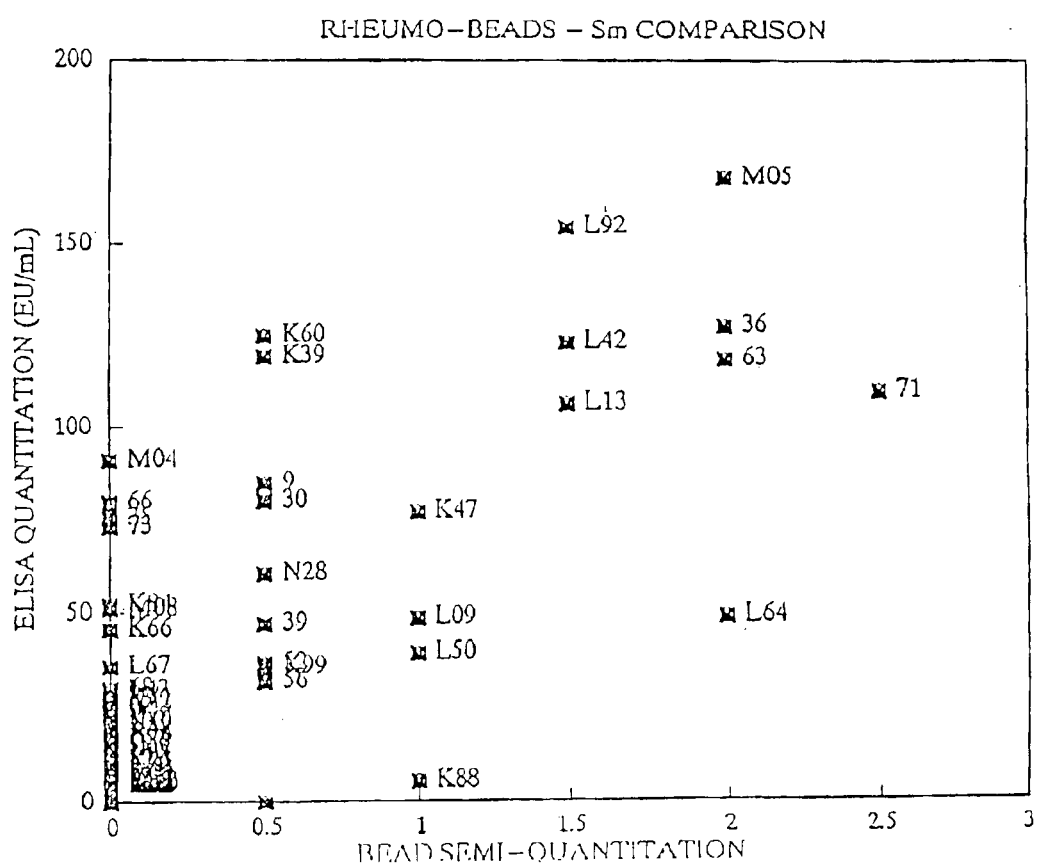
Figure 13:
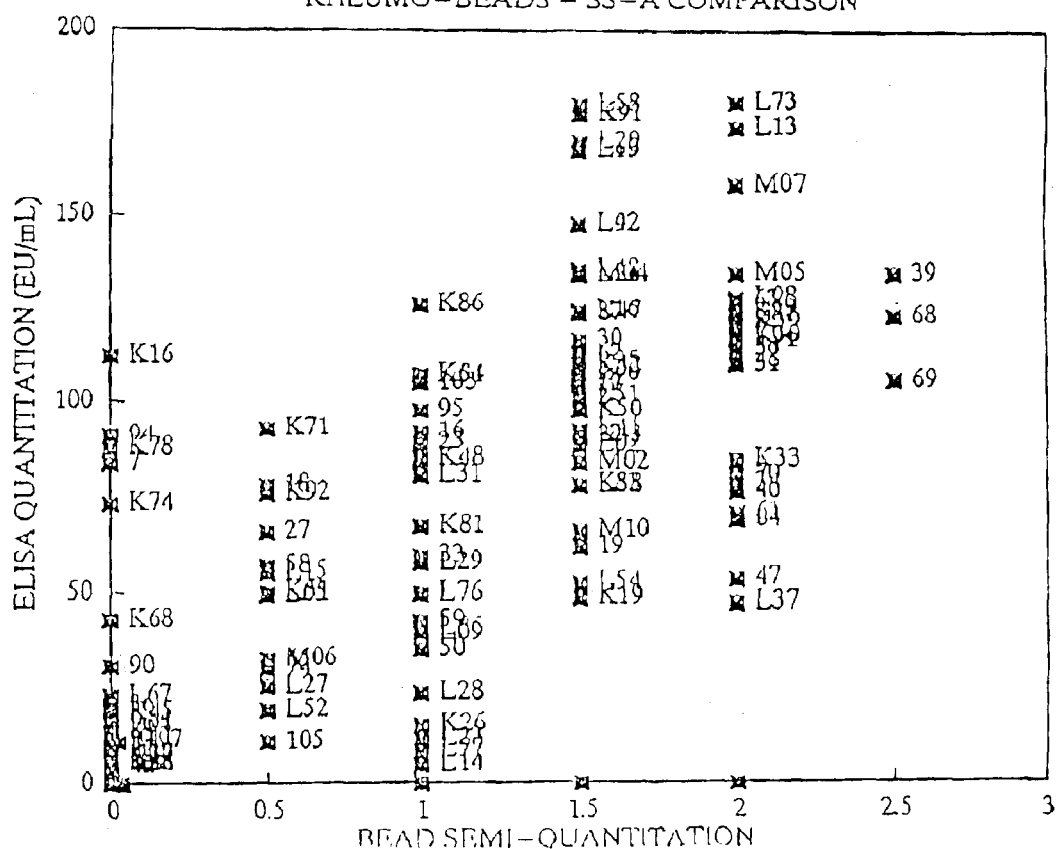
Figure 14:
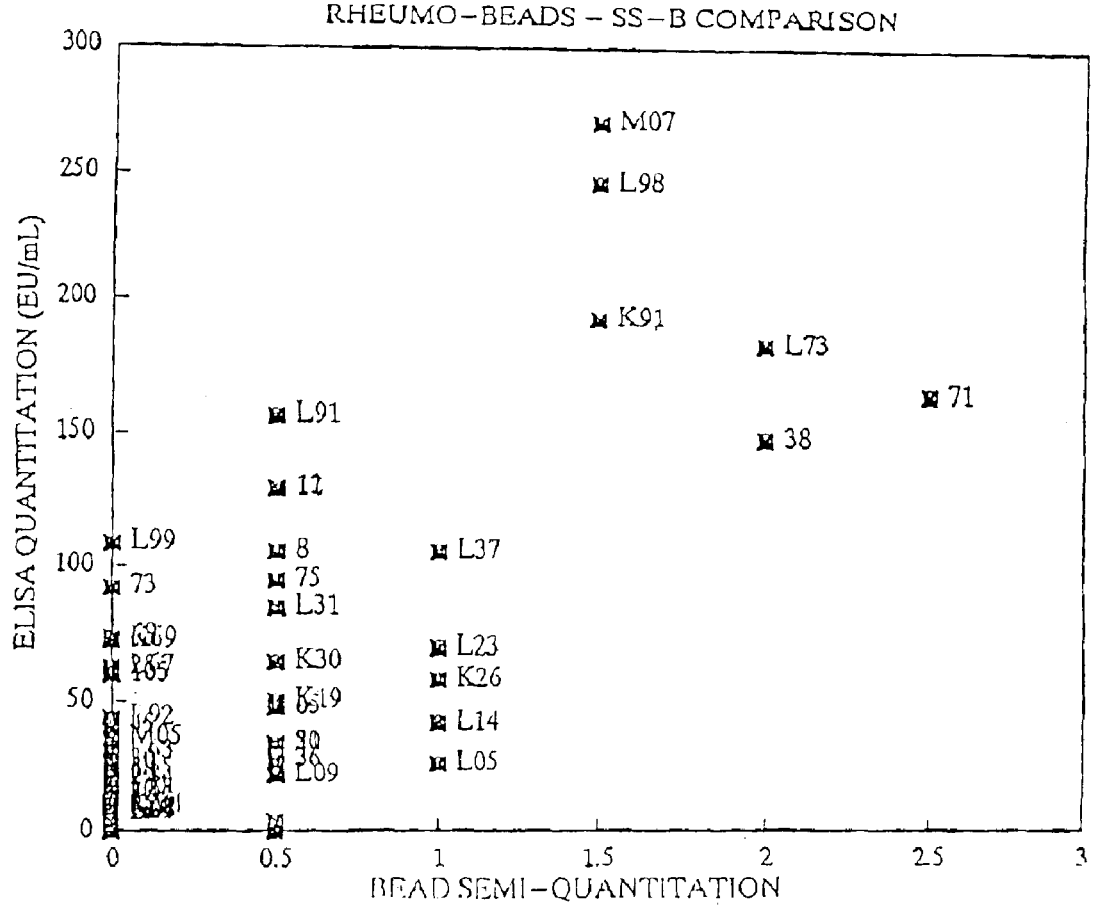
Figure 15:
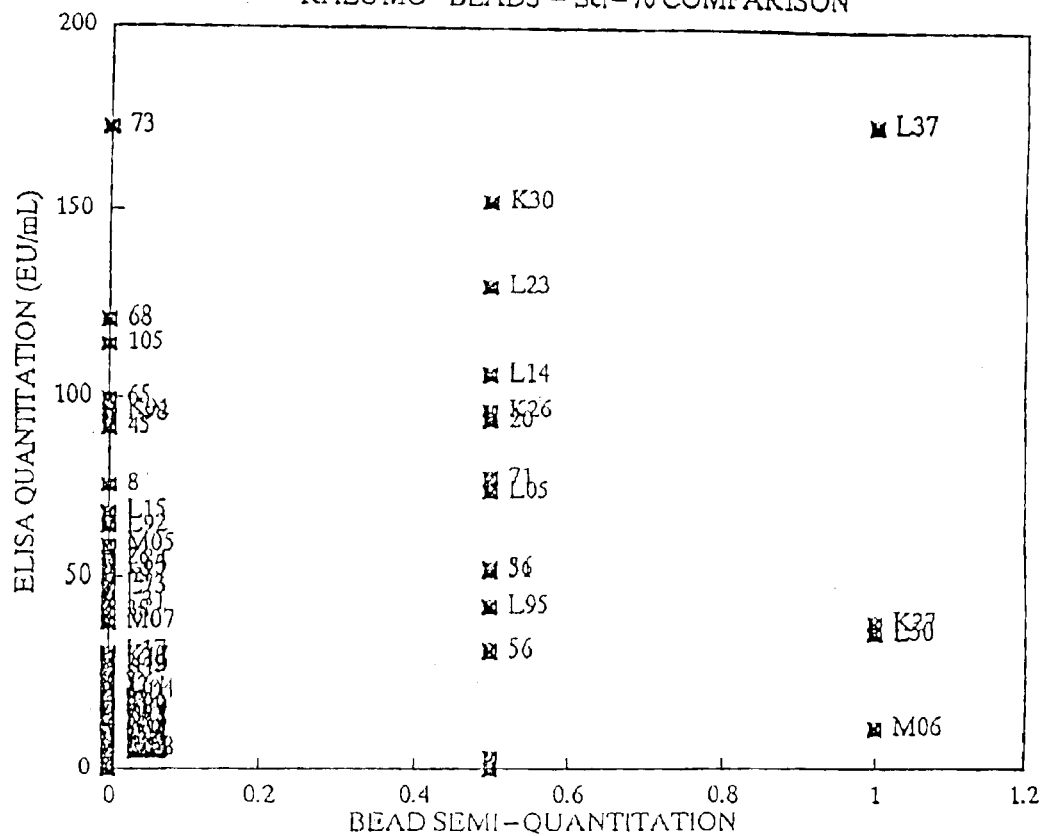
Figure 16:
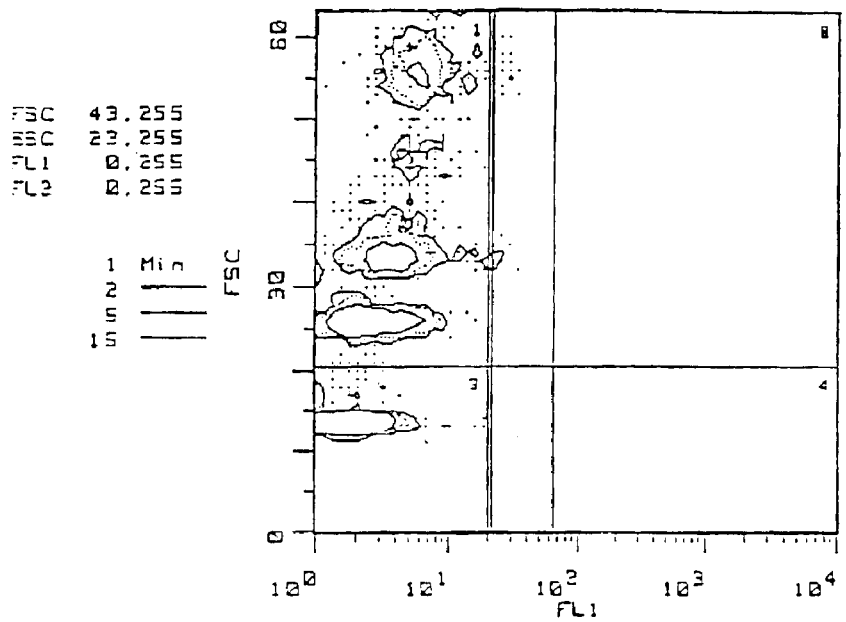
FIGS. 16–22 are graphical and tabular representations of flow cytometer results of seven runs of the double wash bead assay of the present invention using five different sizes of beads each coated with a particular Scl-70, SS-B, SS-A, Sm, and RNP antigen and positive beads labelled with goat anti-human IgG with FITC.
Figure 17:
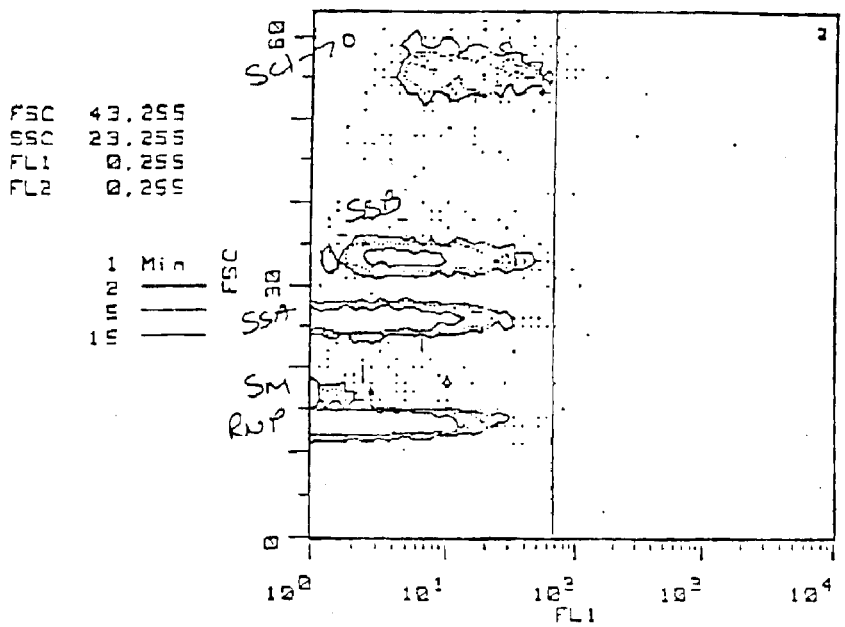
Figure 18:
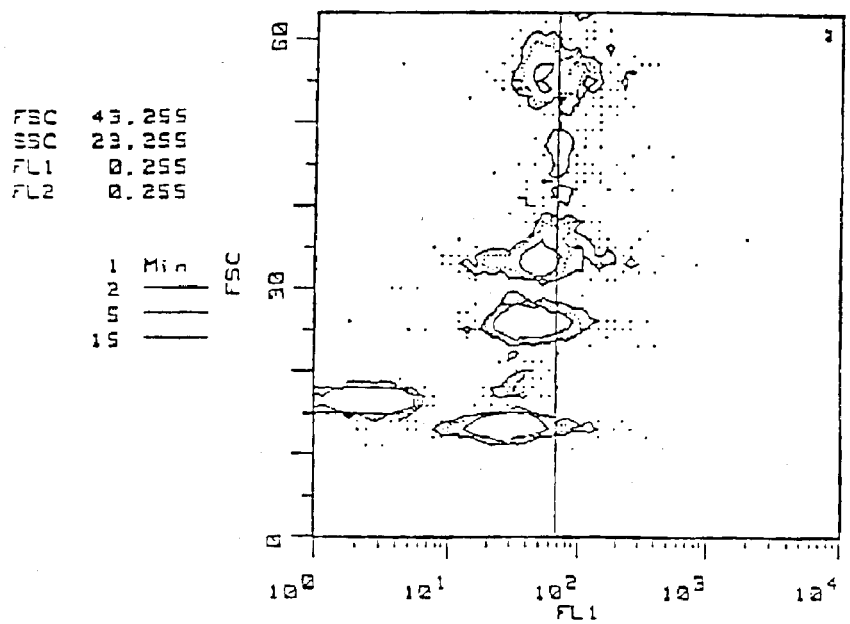
Figure 19:
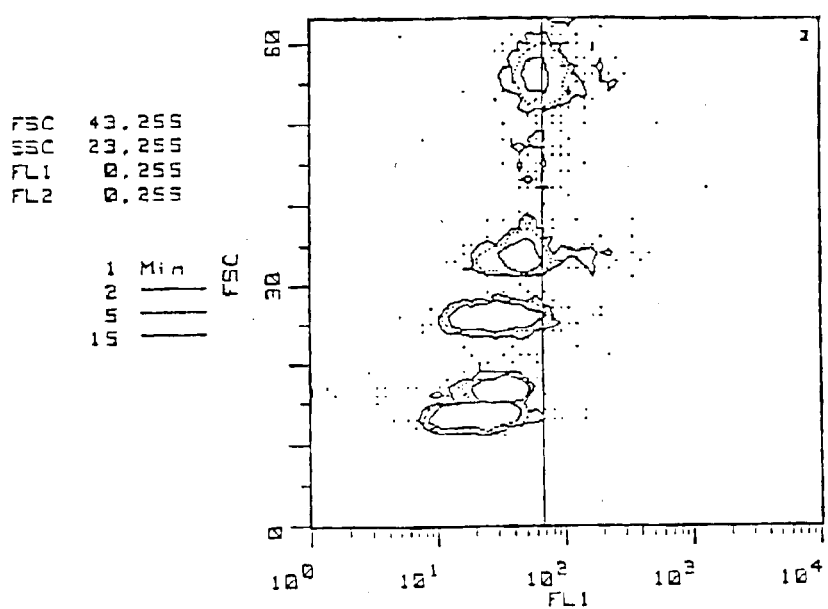
Figure 20:
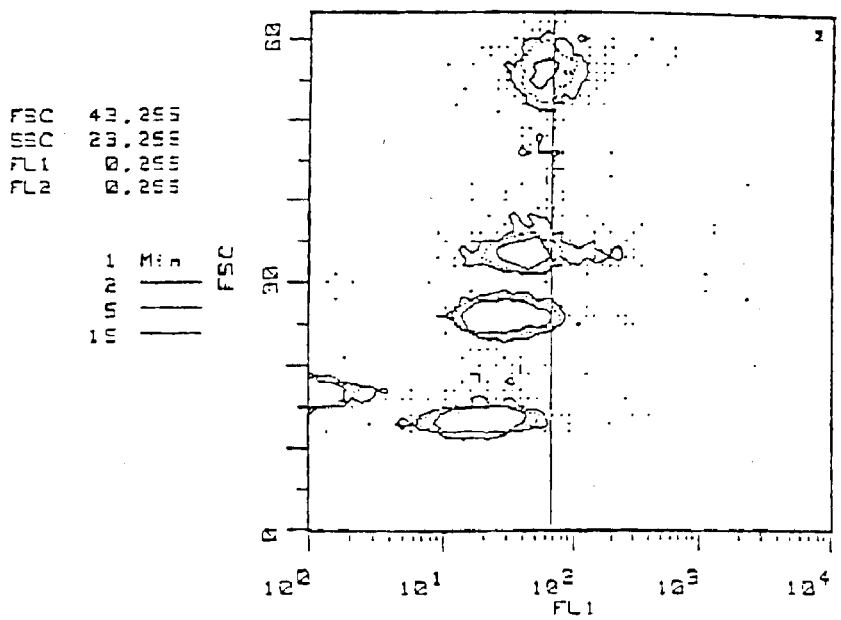
Figure 21:
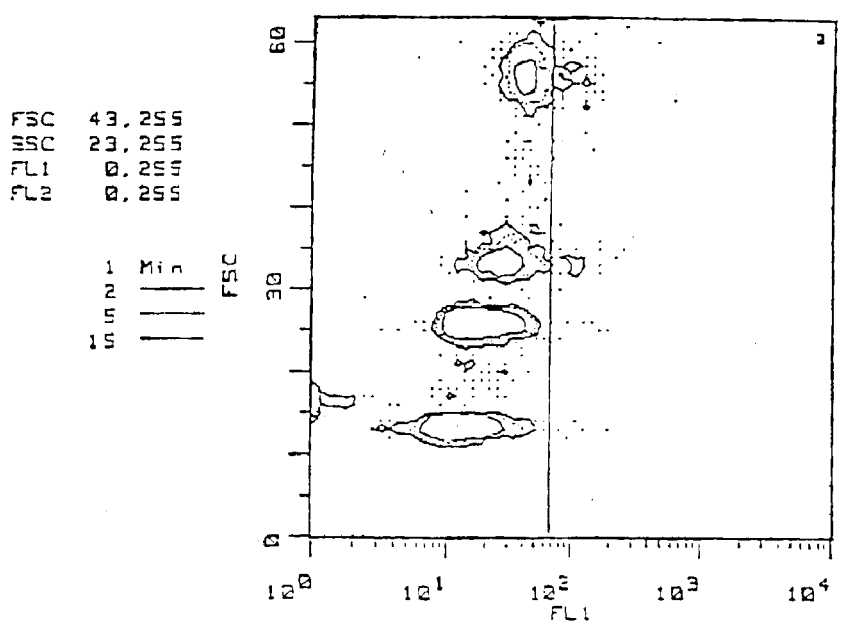
Figure 22:
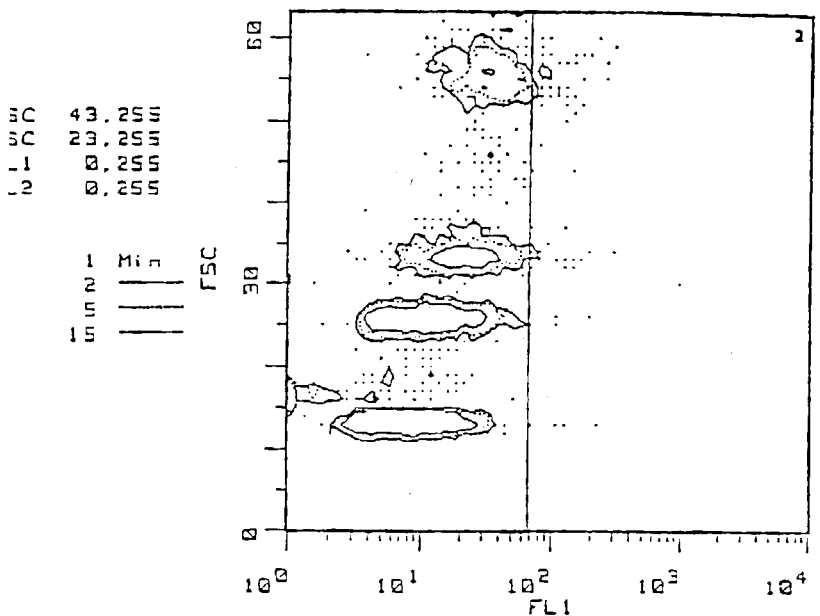

The beads should be evaluated for sensitivity against ELISA assays using known positives quantitated to international standards (EU/mL) All beads should be able to detect antibody concentrations of less then 0.5 EU/mL (See FIG. 10, Sensitivity Graph)

Test Validation Criteria a) The Positive and Negative Controls must be included in each test run as well as a bead blank.
b) The fluorescence intensity of the Positive Control must be 1.5 units or greater.
c) The Negative Control must fall below the 1.5 units.
d) The Positive Control must give a semi-quantitative value within the range for that lot.

If any of these criteria are not met, the results are invalid and the test should be repeated.

Interpretation of Results

The following is a guide to interpretation Each laboratory is encouraged to establish its own "normal" ranges based on populations encountered and flow cytometer sensitivity.

| General Bead Values | Interpretation |
| --- | --- |
| Less than 1.5 units | Negative for antibodies |
| Greater than or equal to 1.5 units and less than 2.0 units | Equivocal for antibodies |
| Greater than or equal to 2.0 units | Positive for antibodies |

Before equivocal results are reported, retest the sample by the above described method or another approved method. Alternatively, obtain another sample from the same patient and retest. If repeated results are still equivocal, the test sample has no significant antibodies and should be reported as negative.

Limitations

The results of the present assay kit should be used in conjunction with clinical criteria for diagnosis of autoimmune rheumatic disease. While laboratory tests should not be used as dictators of therapy, they can be used to supplement clinical observations and as guides to therapy.

In accordance with the present invention it is preferred to use an Becton Dickinson Calibin flow cytometer, but a Coulter XL, or Beaton/Dickinson FCAScan can also be used. All instruments are operated using a 15 mw argon, air-cooled laser and the principles are identical.

Beads sizes may run from about 0.25 $\mu$m to 740.0 $\mu$m.

Other bead materials may include, polystyrene, glass, beads coated with different radical groups, methacrylate-styrene latex, traditional latex, polystyrene DVB. Possible fluorochromes include: Fluorescein isothiocyanate (FITC), Phycoerythrin (PE), Peridinin, Allochlorophyll (Per CP), Allophycocyanin, CY5, Texas Red, Propidium iodide, Ethidium bromides and Acridine orange Antibodies which may be attached to beads or probes to detect antigens in body fluids include any monoclonal antibodies directed at infectious antigens such as, viruses, bacteria, parasites, fungi, and mycoplasma; autoantigens— (cell and cell components, such as nuclei, DNA, RNA nucleoli, membranes); cell products, such as collagen, reticulin, mucus, hormones, cytokines, neurotransmitters, coagulation factors, complement factors, mediators of inflammation (e.g. vasoconstrictive, chemotactic, enzymatic, phospholy), and enzymes; cell membrane antigens (erythrocytes-cross match, HLA-transplantation), and spermatozoa.

Recombinant DNA or RNA may be attached to beads as molecular probes for the detection of infectious agents, particularly viruses (EBV, CMV, HIV, varicella-zoster, hepatitis, HPV, HCV, HBV, HTLV), oncogens and other disease related genes, in fluids by molecular hybridization.

Many of the flow cytometers now have autobiosamplers which utilize robotic arms for multiple sampling. Likewise, the entire procedure may be placed on automated pipettors/dilutors prior to the actual analysis for large scale operations.

Semi-quantitative results can now be achieved by correlating the relative fluorescence to that of a linear fluorescent histogram and determining index cut-off per bead. This is the same for any instrument used. Quantitative results may also be obtained by using pre-analyzed standards at specific EU/mL concentration.

Other Examples of Materials Bound on Beads:
a) Antigens—RnP, Sm, SS-A, SS-B, Scl-70, centromere, Jo-1 HLA blood type
b) Antibodies—anti-p24, anti-htlv, OKT3, anti-platelet
c) Chemicals—IL-2, Toxins, drugs
d) Microorganisms—*E. coli*, HTLV, viruses, bacteria
e) Cell components—IL-2R, Glycoproteins
f) DNA—double stranded complement strands
g) RNA—viral RNA
h) Others—cardiolipin, pollen, metals, recombinant products

EXAMPLE 11

No-wash Anti-viral Screening Assay and Test Kit

In accordance with still another embodiment of the present invention, an FIBA-FCM assay test kit is described as follows.

Summary of Procedure

1. Add 15 $\mu$L of diluted sample to 500 $\mu$L of CMV, EBV, HBsAg, HBc, HTLV, HCV, HIV bead solution. Mix well.
2. Incubate at room temperature for 15–30 minutes.
3. Place one drop of fluorescenated conjugate into each tube.
4. Incubate at room temperature, in the dark, for 15 minutes.
5. Read on flow cytometer.

Intended Use of Kit

For the simultaneous detection of antibodies to the antigens CMV, EBV, HBsAg, HBC, HIV, HTLV, HCV, in serum as an aid in the diagnosis of viral infection.

Summary and Explanation

Current approaches to the detection of antibodies in these diseases are through the use of ELISA or immunodiffusion assays. The above flow cytometry methods as in the anti-ENA assays, shortens turnaround times, decreases technical manipulations, increases sensitivity, eliminates the use of multiple ELISA plates, and decreases laboratory costs.

The above assay is a flow cytometric based procedure intended for the semi-quantitation of antibodies to HBsAg, HBC, EBV, HTLV, HCV, and HIV. The results are reported as index units using linear fluorescence scales derived from the flow cytometers themselves Gradations are strictly standardized against negative and positive controls.

Principle and Procedure

Highly purified (recombinant) CMV, EBV, HIV, HCV, HBsAg, HBC, and HTLV antigens are bound to respective 2, 3, 4, 5, 6, 7 and 10 $\mu$m latex beads and stabilized for extended shelf life. Diluted patient's sera are placed into test tubes containing a mixture of the seven antigen coated beads and incubated. If an antibody is present to the specific antigen (i.e. bead), it will bind to that specific bead. A second incubation with goat anti-human IgG conjugated with fluorescein isothiocyanate (FITC) is carried out. Conjugate will bind immunologically to the anti-antigen human IgG of the antigen-antibody complex, forming a "sandwich" (FIG. 1).

The fluorescence intensity is based on the avidity of the bead/antibody/conjugate binding. The samples are analyzed using flow cytometers having laser excitation wavelengths of 488 nm. Emission wavelengths of 514 nm are detected by photomultipliers which convert the fluorescent analog signals into digital signals two parameter histograms (size (Y-axis) versus fluorescent intensity (X-axis)).

Specimen Collection

Whole-blood (at least 0.5 mL) should be collected in a non-anticoagulated, red top tube by accepted medical techniques. The serum is separated from the clot and refrigerated, 2–8° C., for short-term storage or stored frozen, −20° C., for long-term storage. Avoid multiple freeze-thaw cycles. Specimens containing visible particulate matter should be clarified by ultracentrion before testing. Grossly contaminated specimens should not be used.

Caution: Serum samples should not be heat-inactivated as this may cause false positive results.

Detailed Procedure

Allow test components and patient samples to warm to room temperature before use. Return promptly to refrigerator after use.
1. Properly label sufficient numbers of test tubes to identify positive and negative controls and patient samples.
2. Add 500 μL of bead solution into each of the labelled test tubes.
3. Prepare 1:20 dilutions of the positive and negative controls (unless prediluted in kit), and the patient samples.
4. Mix sample dilutions gently by withdrawing and expelling in a pipette tip.
5. Transfer each diluted control or patient sample into corresponding test tube.
6. Gently vortex and incubate at room temperature (20–30° C.) for 15–30 minutes.
7. Add one drop (50 μL) of fluorescenated conjugate to each tube.
8. Gently vortex and incubate for 15–30 minutes at room temperature in the dark.
9. Analyze on flow cytometer.

NOTE: Analysis should be made within 2 hours of final staining.

EXAMPLE 12

Detection of Acute (IgM) or Convalescent (IgG) Infection

The same example as above, but, however, dual fluorescent labeled conjugates are used for anti-human IgG and anti-human IgM. For example:

α-IgG-FITC→looking for convalescent infections

α-IgM-PI→looking for acute infections

The above may be run simultaneously but analyzed on two separate histograms, one for each color.

EXAMPLE 13

Multiple Fluorescence Bead Assay
1. Determine the amount of latex bead suspension (e.g. # of drop w/mL carbonate buffer) needed to achieve an event count of 900–1000 beads/second on the flow cytometer.
2. Titer antigen (Ag) to appropriate μg/mL and use concentration deemed optimal for maximum mean channel and fluorescence.
3. Add antigen to each respective tube: (μg)

| Antigen (size bead, dye) | Drops/mL Buffer | Ag/mL Buffer |
|---|---|---|
| RNP (4 μm, FITC) | 3 | 30 |
| Sm (5 μm, FITC) | 3 | 10 |
| SS-A (6 μm, FITC) | 6 | 15 |
| SS-B (7 μm, PE) | 6 | 15 |
| Scl-70 (10 μm, PE) | 10 | 10 |

4. Incubate bead/antigen mixture for 12–18 hours at 4–8° C.
5. Centrifuge solution at full speed in a refrigerated centrifuge for 10 minutes.
6. Decant supernatant and gently resuspend beads by hand.
7. Add 1 mL of 0.5% albumin in PBS per mL original volume (optional).
8. Gently vortex.
9. Centrifuge, decant and gently resuspend beads.
10. Add 1 mL of carbonate buffer per original milliliters of antigen/bead solution.
11. Add 100 mL of each antigen/bead mixture to all reaction tubes.
12. Dilute positives negative and patient serum.
13. Add 15 μL of each serum diluted to appropriately labelled tube.
14. Vortex gently and incubate for 15–30 minutes at room temperature.
15. Add 50 μL of goat anti-human IgG F (ab')$^2$-FITC 1.20 (NOTE: dilution may slightly vary from lot to lot, titer all new lots).
16. Gently vortex and incubate 15 minutes at room temperature.
17. Read on flow cytometer.

EXAMPLE 14

Multiple Dye Bead Assay
1. Determine the amount of latex bead suspension (e.g. # of drop w/mL carbonate buffer) needed to achieve an event count of 900–1000 beads/second on the flow cytometer.
2. Titer antigen (Ag) to appropriate μg/mL and use concentration deemed optimal for maximum mean channel and fluorescence.
3. Add a particular antigen to each respective tube (μg)

| Size bead, fluorescent dye | Drops/mL Buffer | Ag/mL Buffer |
|---|---|---|
| 4 μm, PE | 3 | 30 |
| 5 μm, PE | 3 | 10 |
| 6 μm, PE | 6 | 15 |
| 7 μm, FITC | 6 | 15 |
| 10 μm, FITC | 10 | 10 |
| 12 μm, FITC | 10 | 10 |

4. Incubate bead/antigen mixture for 12–18 hours at 4–8° C.
5. Centrifuge solution at full speed in a refrigerated centrifuge for 10 minutes.
6. Decant supernatant and gently resuspend beads by hand.
7. Add 1 mL of 0.5% albumin in PBS per mL original volume.
8. Gently vortex.
9. Repeat steps 5 and 6.
10. Add 1 mL of carbonate buffer per original milliliters of antigen/bead solution.
11. Add 100 mL of each antigen/bead mixture to all reaction tubes.
12. Dilute positive, negative and patient serum.
13. Add 15 μL of each serum diluted to appropriately labelled tube.
14. Vortex gently and incubate for 15–30 minutes at room temperature.
15. Add goat anti-human IgG F (ab')$^2$-FITC 1:20 (NOTE: dilution may slightly vary from lot to lot, titer all new lots).
16. Gently vortex and incubate 15 minutes at room temperature.
17. Read on flow cytometer.

In accordance with an exemplary embodiment of the present invention, coated latex beads, anti-nuclear antibodies, fluorescenated antibodies against such anti-nuclear antibodies, platelets and flow cytometry are combined to provide multiparameter devices, reagents, positive controls, and for the detection and quantification of a plurality of analytes in a single tube.

Figure 25:
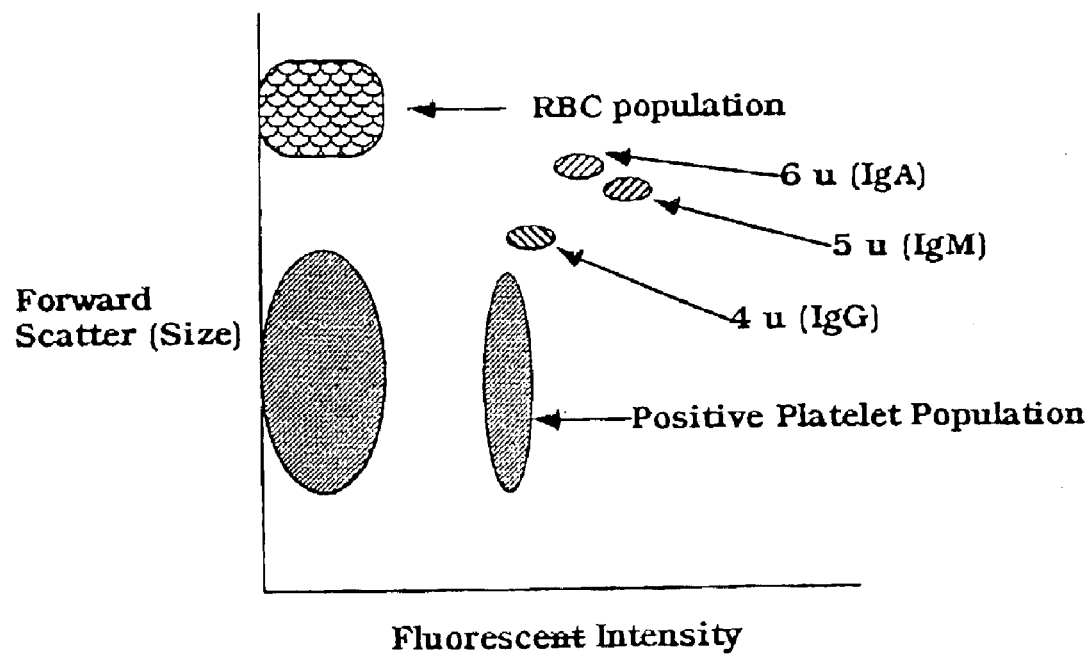
Figure 26:
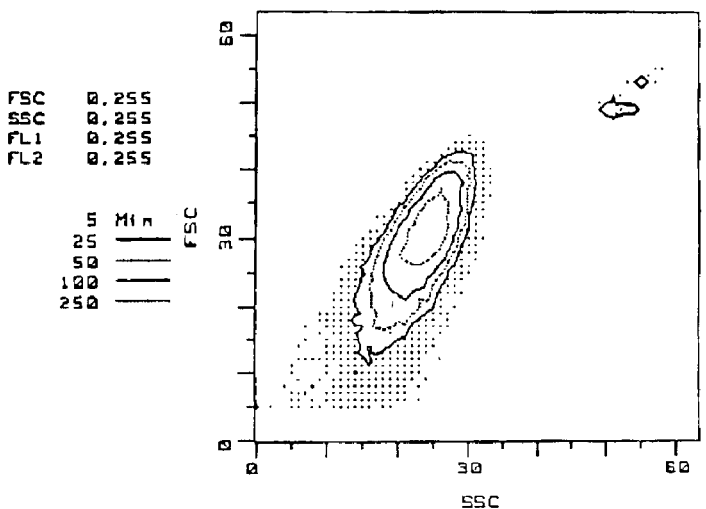
FIGS. 26–32 are graphical and tabular representations of flow cytometer results, histograms or cytograms relating to platelets, reagents and assays.
Figure 27:
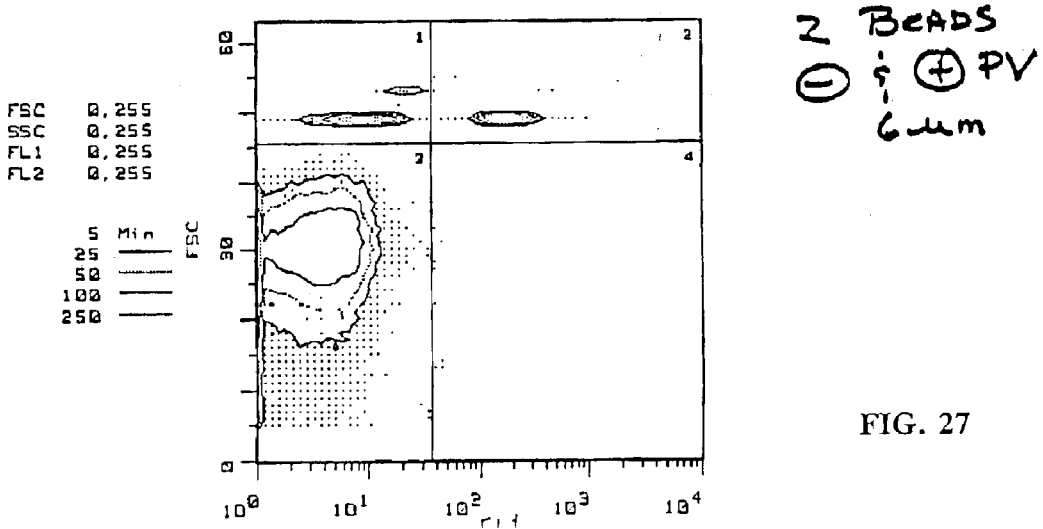
Figure 28:
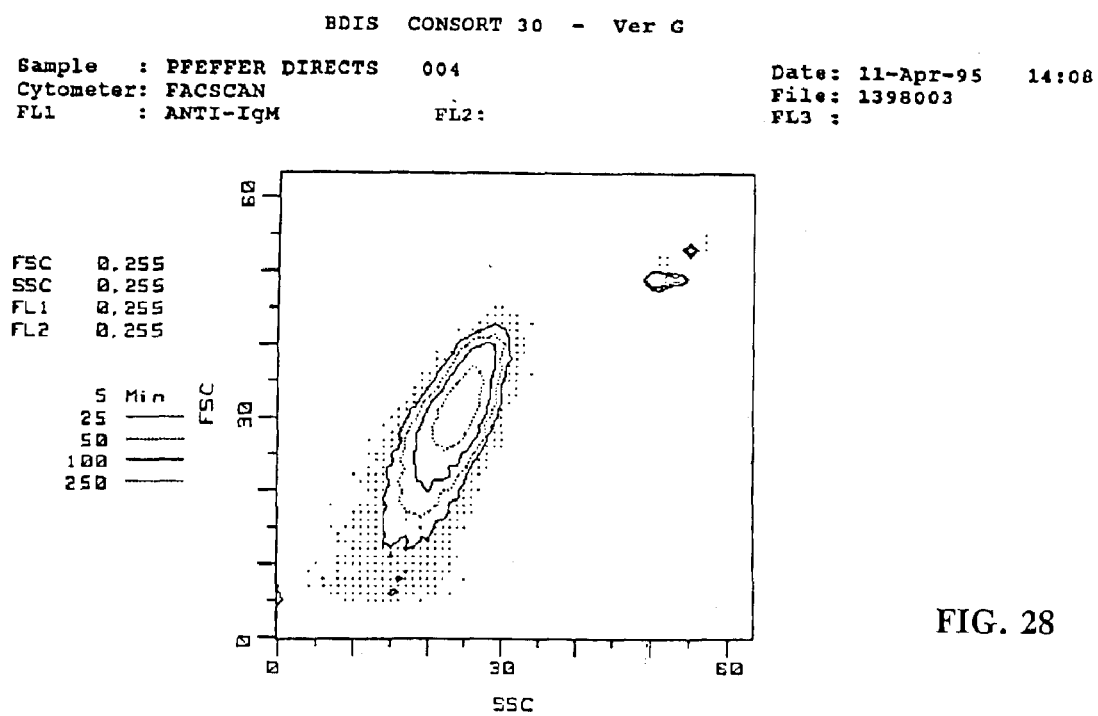
Figure 29:
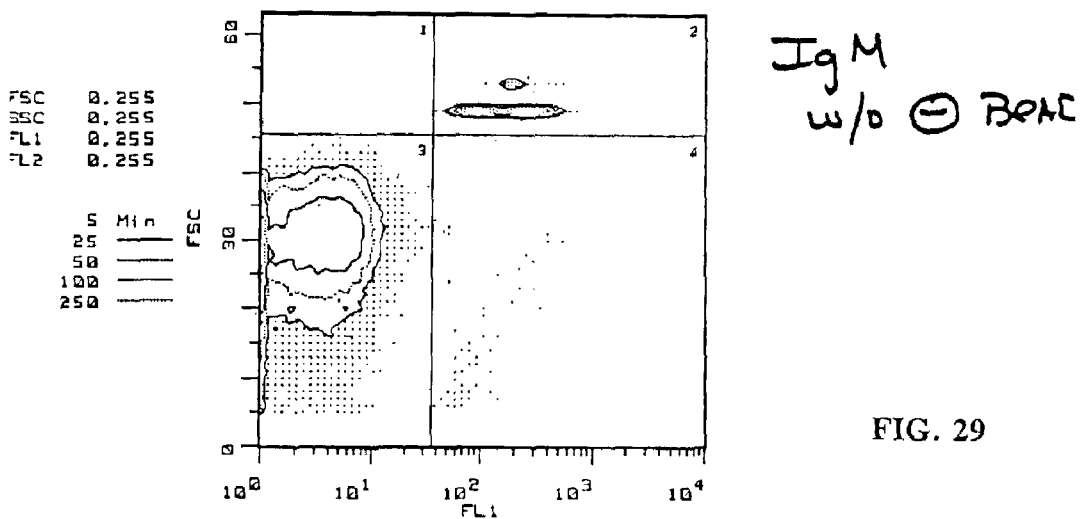
Figure 30:
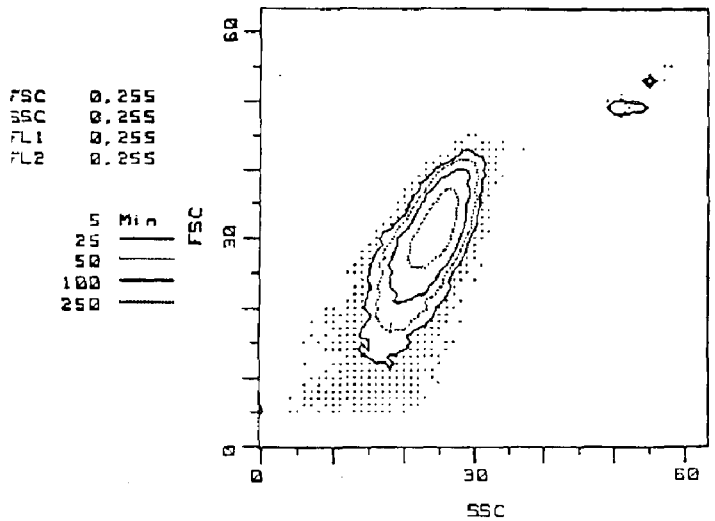
Figure 31:
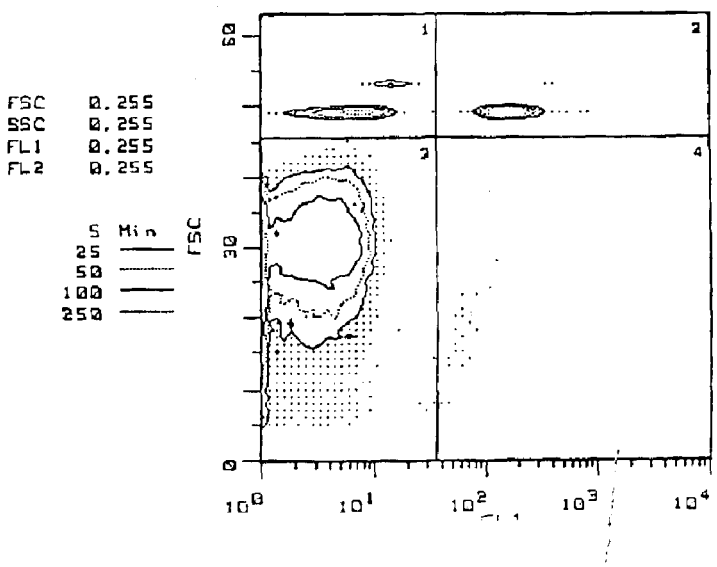
Figure 32:
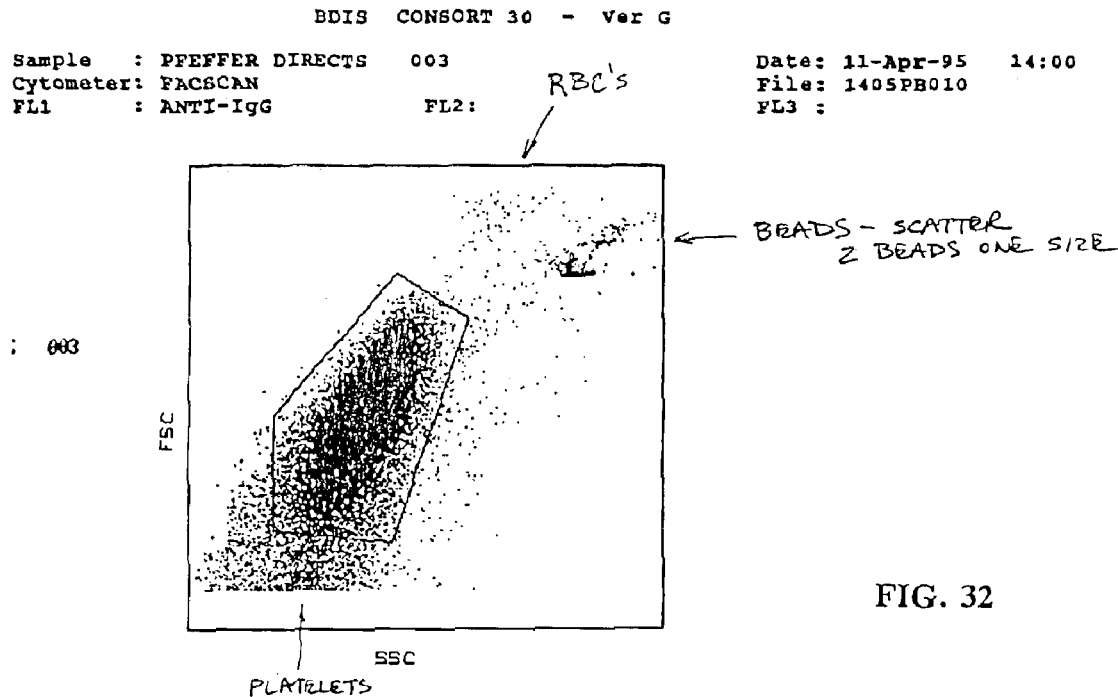

One basic principle of the present invention is to conjugate different antigens or antibodies to the exterior of latex microspheres (beads) of different sizes and to add platelets. The coated microspheres and platelets are used to detect the appropriate specific antibodies, antigens, and platelets simultaneously in one tube and provide a positive reagent control for each patient. The ability to detect multiple analytes in one reaction tube eliminates the variability often seen in results arising from separate assays. Procedurally; latex beads are coated with specific control antigens or antibodies. These beads vary in size and may also contain fluorescent dyes e.g. FITC, PE, etc. One or more of these precoated beads are then incubated with the sample (serum, body fluid) solution including platelets. If an antibody-antibody or antigen-antibody complex has been formed, a 2° indicator fluorochrome labelled antibody will bind to the appropriate bead (FIG. 25).

Figure 23:
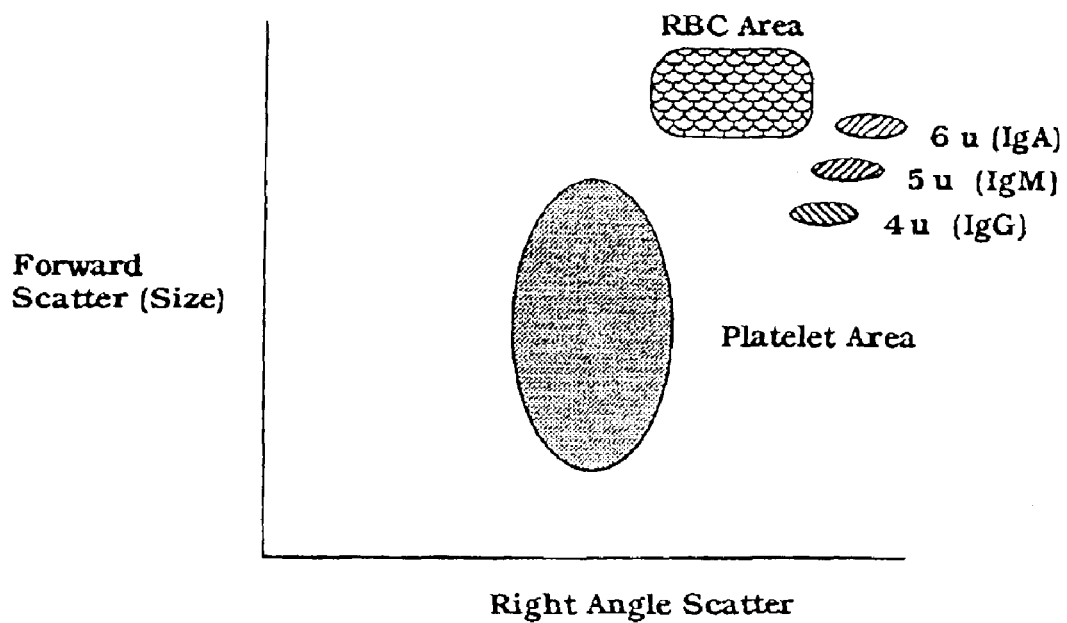
FIGS. 23–25 and 33 are schematic graphical illustrations of flow cytometer results histograms or cytograms relating to a platelet positive control assay and reagent.
Figure 24:
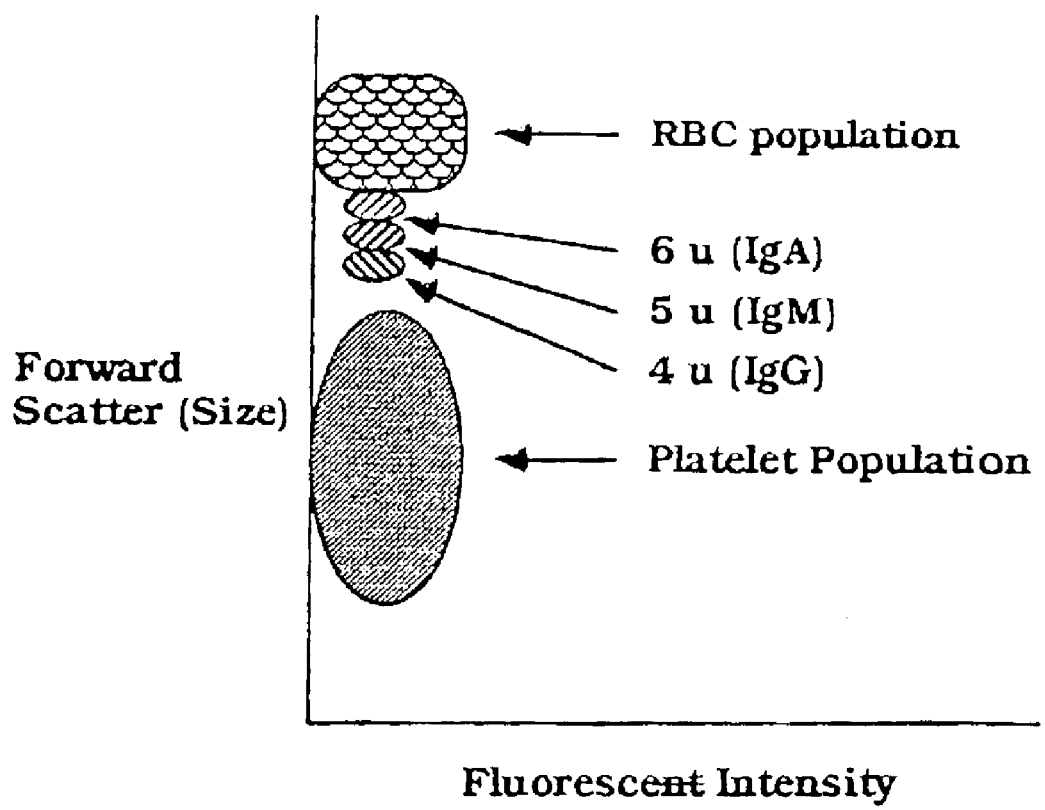

The beads are centrifuged, washed, and analyzed with a flow cytometer using forward angle light scatter to discriminate the different sized beads and platelets, and using fluorescence to detect the presence and quantity. The solution containing beads is passed through a series of tubes until it reaches the optical quartz cell of the flow cytometer. Because of the laminar flow of sheath fluid, single particle analysis is achieved. The signal is converted from analog to a digital display representing the size of the spheres and fluorescence of each (FIG. 25). Controls are used to adjust for the fluorescence background created by electronic and particle noise (FIGS. 23, 24 and 25). A forward scatter (size) adjustment of the multiple sized bead antigen or antibody complexes is necessary in order to semi-quantitate or quantitate the relative concentration of antigen or antibody on the bead surface through single screen, visual distribution. As seen in FIG. 24, a fluorescent threshold (x-axis) is established below which fluorescence values are considered negative. Upon addition of a "positive" sample, (containing appropriate platelet, antibody or antigen) the reaction between the fluorochrome labelled indicator antibody-antigen or antibody-antibody bead complex, amplifies the fluorescence signals detected by the flow cytometer (FIG. 25). Thus, the definition of "positivity" in this system is relative to the negative control (background) and can easily be interpreted.

Multiple analytes including antibodies or antigens can readily be displayed and quantitative values obtained in a single two-dimensional histogram Similarly, additional bead systems can be combined within the size distinguishing capabilities of the flow cytometer and the sizes available from vendors providing latex particles (FIG. 23). As seen in FIG. 25, the multiple antigen or antibody coated bead system incorporates specific anti-species specific 2° antibodies, labelled with fluorochromes (e.g. FITC, PE), to detect the presence of antigen-antibody or antibody-antibody complexes on the beads. All other antibodies non-specifically bound to the latex surface are either washed away or ignored by the indicator antibody.

The present invention uses the principles of flow cytometry and light scatter to detect different sizes of latex particles and platelets with fluorescence as the endpoint. Multiple analytes including antigens or antibodies and platelets in body fluids are detected simultaneously in a single tube because each specific analyte is differentiated by the size of the bead it is bound to and platelets are differentiated by their size.

EXAMPLE 15
Double Wash Positive Control Detection System

In accordance with one example of the present inventions five distinct latex beads each coated with a unique control antigen are incubated with positive antibody control serum and then detected with goat anti-human FITC labelled antibodies. Positivity is distinguished or semi-quantitated using uncoated negative control beads as the negative standard. Forward scatter (forward angle light scatter, FALS, size) versus green fluorescence (FL1) are used to detect positivity.

Purified antigens, positive control sera, human antibodies, monospecific donor plasma; anti-human antibodies, etc. for autoimmune testing are commercially available. For example, vendors produce affinity purified, highly immunospecific, antigens such as Ro(SS-A), La(SS-B), Sm(Smith), Sm/RNP, Scl-70, and Jo-1 as well as purified whole histones and histone subclasses (distinct molecular fractions). ImmunoVision, Inc. also provides positive control sera for autoimmune testing, human antibodies against Ro(SS-A), La(SS-B), Sm, RNP, Scl-70, Jo-1, PM-1, monospecific donor plasma against Cardiolipin, dsDNA, Jo-1, Mitochondrial, PCNA, PM-1, Po, RNP, Scl-70, Sm, Ro(SS-A), La(SS-B), and thyroid microsomal, animal tissue acetone powders, animal sera and immunoglobulin fractions (whole serum, gamma fractions, purified IgG), animal second antibodies (whole antisera, IgG fractions, affinity purified) anti-whole sera, mouse antisera, and whole antisera to selected animal and human proteins.

Materials
3 $\mu$m particle sized latex bead, Duke Scientific, Cat #4203A
4 $\mu$m particle sized latex bead, Duke Scientific, Cat #4204A
5 $\mu$m particle sized latex bead, Duke Scientific, Cat #4205A
6 $\mu$m particle sized latex bead, Duke Scientific, Cat #4206A
7 $\mu$m particle sized latex bead, Duke Scientific, Cat #4207A
8 $\mu$m particle sized latex bead, Duke Scientific, Cat #4210A
Sm/RNP Complex antigen, Immunovision, Cat #SCR-3000
Sm antigen, 1000 units, Immunovision, Cat #SMA-3000
SS-A (Ro) antigen, 1000 units, Immunovision, Cat #SSA-3000
SS-B (La) antigen, 1000 units, Immunovision, Cat #SSB-3000
Scl-70 antigen, 1000 units, Immunovision, Cat #SCL-3000
dsDNA antigen, 1000 units, Immunovision, Cat #dsDNA-3000
Anti-RNP, lyophilyzed, Immunovision, Cat #HRN-0100
Anti-Sm, lyophilyzed, Immunovision, Cat #HSM-0100
Anti-SS-A (Ro) lyophilyzed, Immunovision, Cat #HSA-0100
Anti-SSB (La), lyophilyzed, Immunovision, Cat #HSC-0100
Anti-Scl-70, lyophilyzed, Immunovision, Cat #HSC-0100
Anti-dsDNA, positive sera
Goat anti-human IgG F(ab')$^2$-FITC, Tago, Inc., Cat #4200
Sodium Carbonate, Sigma Chemical, Cat #S-6139
Sodium Bicarbonate, Baker Chemical, Cat #3506–1
Albumin, bovine, Sigma Chemical, Cat #A-7888
200 $\mu$l adjustable pipettor
pipettor tips
10 mL pipettes
Centrifuge
12×75 mL polystyrene test tubes
13 mm caps
flow cytometer
Reagents
Carbonate Buffer, pH 9.6
1. Add 1.5 g of sodium carbonate and 0.8 g of sodium bicarbonate to 500 mL of distilled water.
2. Mix for 5–10 minutes or until all crystals are dissolved.
3. Adjust pH to 9.6 using 2N NaOH.
4. Store at 4–8° C.
5. Buffer only to be used for less than 48 hours after preparation. For antigen coating only.
0.5% albumin, bovine in PBS
1. Mix 0.5 g of bovine albumin in 100 mL of PBS.
2. Mix thoroughly.
3. Store at 4–8° C. for one month.

Procedure
1. Determine the amount of latex bead suspension (e.g. # of drop w/mL carbonate buffer) needed to achieve an event count of 900–1000 beads/second on the flow cytometer.
2. Titer control antigen (Ag) to appropriate µg/mL and use concentration deemed optimal for maximum mean channel and fluorescence.
3. Add antigen to each respective tube: (µg)

| Antigen (size bead) | Drops/mL Buffer | Ag/mL Buffer |
|---|---|---|
| Scl-70 (3 µm) | 2 | 20 |
| RNP (4 µm) | 3 | 30 |
| Sm (5 µm) | 3 | 10 |
| SS-A (6 µm) | 6 | 15 |
| SS-B (7 µm) | 6 | 15 |
| DsDNA (8 µm) | 8 | 10 |

4. Incubate bead/antigen mixture for 12–18 hours at 4–8° C.
5. Centrifuge solution at full speed in a refrigerated centrifuge for 10 minutes.
6. Decant supernatant and gently resuspend beads by hand.
7. Add 1 mL of 0.5% albumin in PBS per mL original volume.
8. Gently vortex.
9. Repeat steps 5 and 6.
10. Add 1 mL of carbonate buffer per original milliliters of antigen/bead solution.
11. Add 100 µL of each antigen/bead mixture to all reaction tubes.
12. Dilute positive serum 1:100 (unless prediluted).
13. Add 15 µL of each positive serum diluted to appropriately labelled tube.
14. Vortex gently and incubate for 15–30 minutes at room temperature.
15. Add 10–50 µL of Goat anti-human IgG F(ab')$_2$-FITC 1:20 (NOTE: dilution may slightly vary from lot to lot. Titer all new lots).
16. Gently vortex and incubate 15 minutes at room temperature.
17. Read on flow cytometer.

EXAMPLE 16
Double Wash Control Detection System

In accordance with yet another example of the assay of the present invention the method follows.
Procedure
1. Determine the amount of latex bead suspension (e.g. # of drop w/mL carbonate buffer) needed to achieve an event count of 900–1000 beads/second on the flow cytometer.
2. Titer positive control antibodies to appropriate µg/mL and use concentration deemed optimal for maximum mean channel and fluorescence.
3. Add positive control human antibody to each respective tube: (µg)

| Antibody (size bead) | Drops/mL Buffer | Ab/mL Buffer |
|---|---|---|
| anti-RNP (660 µm) | 3 | 30 |
| anti-Sm (680 µm) | 3 | 10 |
| anti-SS-A (700 µm) | 6 | 15 |
| anti-SS-B (720 µm) | 6 | 15 |
| anti-Scl-70 (740 µm) | 10 | 10 |

4. Incubate bead/antibody mixture for 12–18 hours at 4–8° C.
5. Centrifuge solution at full speed in a refrigerated centrifuge for 10 minutes.
6. Decant supernatant.
7. Gently resuspend beads by hand.
8. Gently vortex.
9. Repeat steps 5 and 6.
10. Add 1 mL of carbonate buffer per original milliliters of antigen/bead solution.
11. Add 100 mL of each antibody/bead mixture to all reaction tubes.
12. Dilute positive serum 1:20 in PBS.
13. Add 50 µL of each serum diluted to appropriately labelled tube.
14. Vortex gently and incubate for 15 minutes at room temperature.
15. Wash once with 1 mL carbonate buffer.
16. Repeat steps 5 and 6.
17. Add 20 µL of Goat anti-human IgG F(ab')$_2$-FITC 1:20 (NOTE: dilution may slightly vary from lot to lot. Titer all new lots).
18. Gently vortex and incubate 15 minutes at room temperature.
19. Repeat steps 5 and 6.
20. Add 0.5 mL of carbonate buffer.
21. Read on flow cytometer.

EXAMPLE 17
Double Wash Control Detection System

In accordance with still another example of the present invention the assay is as follows.
Procedure
1. Determine the amount of latex bead suspension (e.g. # of drop w/mL carbonate buffer) needed to achieve an event count of 900–1000 beads/second on the flow cytometer.
2. Titer positive control antibodies or Ig to appropriate µg/mL and use concentration deemed optimal for maximum mean channel and fluorescence.
3. Add positive control antibodies or Ig to each respective tube: (µg)

| Antibody (size bead) | Drops/mL Buffer | Ab/mL Buffer |
|---|---|---|
| anti-Sm/RNP (4 µm) | 3 | 30 |
| anti-Jo-1 (5 µm) | 3 | 10 |
| anti-Ro/SS-A (6 µm) | 6 | 15 |
| anti-La/SS-B (7 µm) | 6 | 15 |
| anti-dsDNA (10 µm) | 10 | 10 |

4. Incubate bead/antibody mixture for 12–18 hours at 4–8° C.
5. Centrifuge solution at full speed in a refrigerated centrifuge for 10 minutes.
6. Decant supernatant.
7. Gently resuspend beads by hand.
8. Gently vortex.
9. Repeat steps 5 and 6.
10. Add 1 mL of carbonate buffer per original milliliters of antigen/bead solution.
11. Add 100 mL of each antibody/bead mixture to all reaction tubes.
12. Dilute positive serum 1:20 in PBS.
13. Add 50 µL of each serum diluted and control or patient platelets to appropriately labelled tube.
14. Vortex gently and incubate for 15 minutes at room temperature.
15. Wash once with 1 mL carbonate buffer.
16. Repeat steps 5 and 6.
17. Add 20 µL of Goat anti-human IgG F(ab')$_2$-FITC 1:20 (NOTE: dilution may slightly vary from lot to lot. Titer all new lots).

18. Gently vortex and incubate 15 minutes at room temperature.
19. Repeat steps 5 and 6.
20. Add 0.5 mL of carbonate buffer.
21. Read on flow cytometer.

EXAMPLE 18
Double Wash Anti-platelet Ig Control Detection System

In accordance with another example of the present invention the multiple parameter bead assay is as follows.
Procedure
1. Determine the amount of latex bead suspension (e.g. # of drop w/mL carbonate buffer) needed to achieve an event count of 900–1000 beads/second on the flow cytometer.
2. Titer human immunoglobulins (Igs) to appropriate μg/mL and use concentration deemed optimal for maximum mean channel and fluorescence.
3. Add positive control Ig (μg) to each respective tube:

| size bead | Drops beads/mL Buffer | μg Ig/mL Buffer |
|---|---|---|
| IgG (4 μm) | 3 | 30 |
| IgA (6 μm) | 6 | 15 |
| IgM (10 μm) | 10 | 10 |

4. Incubate bead/Ig mixture for 12–18 hours at 4–8° C.
5. Centrifuge solution at full speed in a refrigerated centrifuge for 10 minutes.
6. Decant supernatant.
7. Gently resuspend beads by hand.
8. Gently vortex.
9. Repeat steps 5 and 6.
10. Add 1 mL of carbonate buffer per original milliliters of Ig/bead solution.
11. Add 100 mL of each Ig/bead mixture to all reaction tubes.
12. Dilute positive serum 1:20 in PBS.
13. Add 15–50 μL of each serum diluted and control or patient platelets to appropriately labelled tube.
14. Vortex gently and incubate for 15–30 minutes at room temperature.
15. Wash once with 1 mL saline.
16. Repeat steps 5 and 6.
17. Add Goat anti-human IgG F (ab')$^2$-FITC 1:20 (NOTE: dilution may slightly vary from lot to lot. Titer all new lots).
18. Gently vortex and incubate 15–30 minutes at room temperature.
19. Repeat steps 5 and 6.
20. Add 0.5 mL of carbonate buffer.
21. Read on flow cytometer.

It has been demonstrated that immunoglobulin (Ig) can be attached to latex beads (FIGS. 26–31). After incubation with fluorescenated anti-human IgG and/or platelets, beads that have bound antibody fluoresce and/or platelets are specifically detectable because of their size differences (FIGS. 23–33).

The results of the control assays of the present invention are improved by determining: 1) optimal concentrations of analytes including antigens, antibodies or Ig on latex microspheres using block titration methods; 2) optimal ratios of serum or platelets to bead concentrations; and 3) optimal concentrations of secondary antibody (anti-human IgG). Once optimal bead, analyte, antigen, antibody, and/or platelet concentrations are determined and, using commercially available control analytes, antigens, antibodies, Ig, platelets, and patient platelets sera containing these analytes, antibodies, antigens, platelets coated beads are incubated with various dilutions of sera, platelets and secondary (detector) antibody. Several dilutions of known positive sera and platelets can be performed to determine the sensitivity of the assay for each patient.

Further, replicates should be performed on an automated system, e.g. the Becton Dickinson Calibin with an autoloaders to determine reproducibility. Stability of analytes, reagents, coated beads, etc. is determined by a longitudinal study in which they are tested for reactivity to the same sera at monthly intervals for at least six months.

Each FIBA-FCM assay kit of the present invention should be tested in multiple clinical flow cytometry laboratories, using the same positive and negative sera and platelets to determine inter-laboratory variation.

The positive control methodology of the present invention provides that platelets and microsphere sizes can be combined with two color FCM and results displayed three dimensionally as a "cloud" display (FIG. 8). This increases the number of analytes, platelets, antibodies or antigens to be simultaneously analyzed (FIG. 9).

EXAMPLE 19
Multiple Parameter Control Reagent and Assay

In accordance with another embodiment of the present invention, positive control IgG, IgM, and IgA are bound to 4, 6 and 10 μm latex beads, respectively and stabilized for extended shelf life. Then, an incubation with goat anti-human IgG, conjugated with fluorescein isothiocyanate (FITC), is carried out. This conjugate will bind immunologically to the Ig on the beads, forming a "sandwich" consisting of bead—Ig—2° antibody—FITC.

Unbound conjugate is removed in the subsequent washing step. The fluorescence intensity is based on the avidity of the bead/antibody/conjugate binding. The samples are analyzed using flow cytometers having laser excitation wavelengths of 488 nm. Emission wavelengths of 514 nm are detected by photomultipliers which convert the fluorescent analog signals into two parameter histograms expressing forward light scatter (Y-axis) versus fluorescence intensity (X-axis, FIG. 25).

Procedure
1. Determine which Ig coating buffer (either carbonate buffer or phosphate buffered saline, PBS) yields highest binding capacity to latex beads. Optimal concentration of beads needs to be determined in order for the flow cytometer to count accurately.
2. Establish titers of both Ig and antibody against the coated beads and run several experiments to maximize signals obtained at different Ig concentrations (mean channel fluorescence).
3. Incubate Ig/bead mixture for several minutes (time to be determined) and wash with either carbonate buffer or PBS.
4. Wash Ig coated beads in buffer (PBS or 0.5% Tween 20 in PBS or carbonate buffer).
5. Determine the background of unlabelled beads.
6. If background exists, decrease to near baseline values.
7. Find proper dilution of labelled goat-anti-human F (ab')$^2$ antibody by titration and add to coated beads.
8. Incubate for optimal time (to be determined) and wash with buffer (PBS or carbonate buffer).
9. Add 1 mL of buffer (PBS or carbonate buffer).
10. Read on flow cytometer.

Quality Control

Negative and positive controls are conducted in each assay. During development all patient samples are tested in parallel by a conventional ELISA method. Reagents are used only during established shelf-lives.

EXAMPLE 20

Multiple Parameter Control System

In accordance with one embodiment of the present invention, one or more control antigens are bound to one or more μm latex beads, respectively and stabilized for extended shelf life. Diluted control serum is placed into test tubes containing a mixture of the control antigen coated beads and incubated. If a control antibody is present for a specific antigen, it will bind to that specific bead. After washing the control bead/serum mixture, a second incubation with anti-human IgG, conjugated with fluorescein isothiocyanate (FITC) is carried out. This conjugate will bind immunologically to the anti-antigen IgG of the antigen-antibody complex, forming a "sandwich" consisting of bead—antigen—1° antibody—2° antibody—FITC (FIG. 1).

Unbound conjugate is removed in the subsequent washing step. Patient or control platelets can be added. The fluorescence intensity is based on the avidity of the bead/antibody/conjugate binding. The control samples are analyzed using flow cytometers having laser excitation wavelengths of 488 nm. Emission wavelengths of 514 nm are detected by photomultipliers which convert the fluorescent analog signals into at least two parameter histograms expressing forward light scatter (Y-axis) versus fluorescence intensity (X-axis, FIG. 2).

EXAMPLE 21

In accordance with another embodiment of the present invention, a "no wash" control immunoassay or immunobead-flow cytometry, control antigens, antibodies, and/or Ig are bound to the same or different sized μm latex beads, respectively and stabilized for extended shelf life. Diluted control serum is placed into the test tubes containing the coated beads and incubated. If an antibody is present for a specific antigen, antibody or Ig, it will bind to that specific bead. Next, a dilution of goat anti-human IgG-FITC in PBS is added to all tubes and a second incubation is carried out. This conjugate will bind immunologically to the anti-antigen Ig of the antigen-antibody complex, or Ig forming a "sandwich" consisting of bead—antigen—1° antibody—2° antibody—FITC (FIG. 1) or bead—Ig—Antibody—FITC. Control or patient platelets are added to respective tubes. Then, PBS is added and the samples are analyzed on a flow cytometer.

EXAMPLE 22

One Step No Wash Control System

The following "no wash" procedure is a modification of the above bead evaluation method.
1. Allow reagents to come to room temperature.
2. Gently invert antigen, antibody, Ig, bacteria, virus, or other analyte coated bead mixture until an even distribution of bead product is observed.
3. Label test tubes for Blank, Controls, and Patients.
4. Add 500 μL of multiple bead suspension to each tube.
5. Dilute patient and control serum 1.20 in isotonic saline (e.g. 10 μL serum to 190 μL saline).
6. Add 50 μL of diluted serum to appropriate test tubes.
7. Add 50 μL of saline to blank tube.
8. Gently vortex and incubate for 15 minutes at room temperature.
9. Make a 1:5 dilution of goat anti-human F (ab')$_2$ IgG FITC (or other fluorochrome) in 0.5% albumin in PBS.
10. Add 50 μL of diluted conjugate to each tube.
11. Add patient platelets or control platelets to appropriate test tubes.
12. Gently vortex and incubate for 15 minutes at room temperatures, in the dark.
13. Add 1 mL of PBS to each tube.
14. Analyze on flow cytometer.

EXAMPLE 23

No Wash Control System
1. Allow reagents to come to room temperature.
2. Gently invert Ig coated bead mixture until an even distribution of bead product is observed.
3. Label test tubes for Blank, Positive Control, and Negative Control.
4. Add at least 200 μL of bead suspension to each tube.
5. Dilute patient and control platelets at least 1.0 in saline.
6. Add at least 10 μL of diluted platelets to appropriate test tubes.
7. Add at least 10 μL of PBS to blank tube.
8. Gently vortex and incubate for at least 5 minutes at room temperature.
9. Make an at least 1:2 dilution of labelled anti-human antibodies in PBS.
10. Add at least 10 μL of diluted conjugate to each tube.
11. Gently vortex and incubate for at least 5 minutes at room temperatures in the dark.
12. Add about 1 mL of PBS to each tube.
13. Analyze on flow cytometer.

EXAMPLE 24

No Wash Control System
1. Allow reagents to come to room temperature.
2. Gently invert Ig coated bead mixture until an even distribution of bead product is observed.
3. Label test tubes for Blanks Positive Control, and Patient Control.
4. Add equal quantities of bead suspension to each tube.
5. Dilute patient and control platelets to about 1:20 in saline (e.g. 10 μL platelets to 190 μL saline).
6. Add equal quantities of diluted platelets to appropriate test tubes.
7. Add the same quantity of PBS to blank tube.
8. Gently vortex and incubate at room temperature.
9. Make an about 1:5 dilution of labelled anti-human antibody in PBS.
10. Add equal quantities of diluted conjugate to each tube.
11. Gently vortex and incubate at room temperature.
12. Add equal quantities of PBS to each tube.
13. Analyze on flow cytometer.

EXAMPLE 25

Anti-SLE Screening Assay Positive Control

In accordance with still another embodiment of the present invention, an FIBA-FCM assay positive control is described as follows.

Summary of Procedure
1. Add 15 μL of diluted control serum (human antibodies against the selected antigens) to 600 μL of RNP, Sm, SS-A(Ro), SS-B(La), dsDNA and Scl-70 coated bead solution and mix well.
2. Incubate at room temperature for 15–30 minutes.
3. Add 1 mL PBS to each tube.
4. Centrifuge tubes for 10 minutes at 1500 g.
5. Decant supernatant and gently resuspend bead pellet.
6. Place one drop of fluorescenated conjugate into each tube and mix well.
7. Incubate at room temperature, in the dark, for 15–30 minutes
8. Add control platelets or patient platelets to appropriate tubes and add 1 mL PBS to each tube.

9. Centrifuge for 10 minutes at 1500 g.
10. Decant supernatant and gently resuspend bead pellet.
11. Add 1 mL of PBS.
12. Read on flow cytometer.

Intended use of Positive Control

For the simultaneous detection of the positive fluorescence values of platelets and of anti-antibodies to the antibodies against the antigens RNP, Sm, SS-A(Ro), SS-B (La), dsDNA and Scl-70 in serum as an aid in the setting of the positive reading region for each patient.

EXAMPLE 26

Highly purified bacterial antigen are bound to respective different sized $\mu$m latex beads and stabilized for extended shelf life. Diluted patient's sera are placed into test tubes containing a mixture of the antigen coated beads and incubated. If an antibody is present to the specific antigen (i.e. bead), it will bind to that specific bead. After washing the bead/sera mixture to remove residual sample, a second incubation with goat anti-human IgG conjugated with fluorescein isothiocyanate (FITC) is carried out. Conjugate will bind immunologically to the anti-antigen IgG of the antigen-antibody complex, forming a "sandwich" (FIG. 1).

Unbound conjugate is removed in the subsequent washing step. The fluorescence intensity is based on the avidity of the bead/antibody/conjugate binding. The samples are analyzed using flow cytometers having laser excitation wavelengths of 488 nm. Emission wavelengths of 514 nm are detected by photomultipliers which convert the fluorescent analog signals into digital signals two parameter histograms (size (Y-axis) versus fluorescent intensity (X-axis, FIG. 2).

When testing with platelets, $\mu$m beads sizes should run from about 0.25 $\mu$m to 1.5 $\mu$m and 3.5 $\mu$m to 740.0 $\mu$m.

Other bead materials may include, polystyrene, glass, beads coated with different radical groups, methacrylate-styrene latex, traditional latex, polystyrene DVB. Possible fluorochromes include: Fluorescein isothiocyanate (FITC), Phycoerythrin (PE), Peridinin, Allochlorophyll (Per CP), Allophycocyanin, CY5, Texas Red, Propidium iodide, Ethidium bromide, and Acridine orange Antibodies which may be attached to beads or probes to detect antigens in body fluids include any monoclonal antibodies directed at infectious antigens such as, viruses, bacteria, parasites, fungi, and mycoplasma; autoantigens—(cell and cell components, such as nuclei, DNA, RNA nucleoli, membranes); cell products, such as collagen, reticulin, mucus, hormones, cytokines, neurotransmitters, coagulation factors, complement factors, mediators of inflammation (e.g. vasoconstrictive, chemotactic, enzymatic, phospholy), and enzymes; cell membrane antigens (erythrocytes-cross match, HLA-transplantation), and spermatozoa.

DNA or RNA may be attached to beads as molecular probes for the detection of infectious agents, particularly viruses (EBV, CMV, HIV, varicella-zoster, hepatitis, HPV, HCV, HBV, HTLV), oncogens and other disease related genes, in fluids by molecular hybridization.

Other Examples of Materials Bound on Control Beads:
a) Antigens—RnP, Sm, SS-A, SS-B, Scl-70
b) Antibodies—anti-p24, anti-htlv, OKT3
c) Chemicals—IL-2, Toxins, drugs
d) Microorganisms—*E. coli*, HTLV, viruses
e) Cell components—IL-2R, Glycoproteins
f) DNA—double stranded complement strands
g) RNA—viral RNA
h) Others—cardiolipin, pollens metals, recombinant products.

EXAMPLE 27

No-wash Anti-viral Control Assay

In accordance with still another embodiment of the present invention, an FIBA-FCM control assay is described as follows Summary of Procedure
1. Add 50 $\mu$L of positives negative or patient control sera to respective tubes of 500 $\mu$L of CMV, EBV, HBsAg, HBc, HTLV, HCV, HIV bead solution. Mix well.
2. Incubate at room temperature for 15 minutes.
3. Place one drop of fluorescenated conjugate into each tube. Mix well.
4. Incubate at room temperatures in the dark, for 15–30 minutes.
5. Read on flow cytometer.

Intended Use of Assay

For the detection of positives negative and patient control values as an aid in the setting of the positive fluorescence region for each patient.

EXAMPLE 28

Highly purified analytes are bound to respective $\mu$m latex beads having a diameter of greater than about 2.0 $\mu$m and stabilized for extended shelf life. Diluted control and patient's platelets are placed into selected test tubes containing a mixture of analyte coated beads and incubated. Next, an incubation with goat Ig-FITC or goat anti-human Ig-FITC is carried out.

Unbound conjugate is removed in the subsequent washing step The fluorescence intensity is based on the avidity of the bead/analyte/conjugate binding. The samples are analyzed using flow cytometers having laser excitation wavelengths of 488 nm. Emission wavelengths of 514 nm are detected by photomultipliers which convert the fluorescent analog signals into digital signals two parameter histograms (size, Y-axis) versus fluorescent intensity (X-axis).

EXAMPLE 29

Multiple Dye Bead Control and Assay
1. Determine the amount of latex bead suspension (e.g. # of drop w/mL carbonate buffer) needed to achieve an event count of 500–1000 beads/second on the flow cytometer.
2. Titer analytes (An) and platelets to appropriate $\mu$g/mL and use concentration deemed optimal for maximum mean channel and fluorescence.
3. Add a particular analyte to each respective tube ($\mu$g)

| Size bead, fluorescent impregnated dye | Drops Beads/mL Buffer | An/uL Buffer |
|---|---|---|
| 4 $\mu$m, PE | 3 | 30 |
| 5 $\mu$m, PE | 3 | 10 |
| 6 $\mu$m, PE | 6 | 15 |
| 7 $\mu$m, FITC | 6 | 15 |
| 10 $\mu$m, FITC | 10 | 10 |
| 12 $\mu$m, FITC | 10 | 10 |

4. Incubate bead/analyte mixture for 12–18 hours at 4–8° C.
5. Centrifuge solution at full speed in a refrigerated centrifuge for 10 minutes.
6. Decant supernatant and gently resuspend beads by hand.
7. Add 1 mL of control or patient platelets to appropriate tubes.
8. Gently vortex.
9. Repeat steps 5 and 6.
10. Add 1 mL of carbonate buffer per original milliliters of analyte/bead solution.

11. Add 100 mL of each analyte/bead or analyte/bead/platelet mixture to respective reaction tubes.
12. Dilute positives negative and patient serum 1:20 in PBS.
13. Add 50 µL of each serum diluted to appropriately labelled tube.
14. Vortex gently and incubate for 15 minutes at room temperature.
15. Wash once with 1 mL carbonate buffer.
16. Repeat steps 5 and 6.
17. Add 20 µL of goat Ig-FITC or goat anti-human IgG F(ab')$_2$-FITC 1:20 (NOTE: dilution may slightly vary from lot to lot, titer all new lots).
18. Gently vortex and incubate 15 minutes at room temperature.
19. Repeat steps 5 and 6.
20. Add 0.5 mL of carbonate buffer.
21. Read on flow cytometer.

FIGS. 26–32 are histograms or cytograms of the bead or beads used with Type O platelets, platelets from a negative patient and a positive patient. When interpreting these cytograms, review the Type O map (FIGS. 23 and 32) for positioning of the beads relative to the cellular populations. The immunoglobulin (Ig) coating for IgG, M, and A is one polyvalent coated bead of 6 µm (as illustrated in the Forward Scatter versus Side Scatter cytograms). A negative, non-coated bead of the same 6µm size is also added as the negative control indicator. This system works in the IgG, A, and M systems separately (see FIGS. 27, 29 and 31). The negative bead has been eliminated from the IgM tube in order to demonstrate that intensity remains constant without any non-coated beads Some doublets do occur as an artifact. These are attributed to the substrate and do not interfere with the main purpose of the reagent and assay.

EXAMPLE 30

Ig Positive Control
Direct Procedure:
1. Add 100 µL of Ig control material to each of three tubes labeled IgG, M and A, respectively.
2. Add patient and control platelets to control, IgG, M and A tubes, respectively.
3. Add goat Ig-FITC to control or specific goat anti-human Ig-FITC, at proper concentrations to IgG, M and A tubes, respectively.
4. Incubate for 15–30 minutes in the dark.
5. Wash once with saline and add 1 mL to final volume.
6. Read on flow cytometer using Fwd Scatter versus FL1.
7. Set positive region based on Control tube for that patient.

EXAMPLE 31

Ig Positive Control
Indirect Procedure:
1. Incubate Type O platelets with 100 µL of diluted control or patient serum in tubes labeled Control, IgG, M and A.
2. After 15–30 minutes, wash tubes with 1 mL of saline.
3. Decant and gently vortex.
4. Add 100 µL of Ig control material to each tube labeled IgG, M and A, respectively.
5. Add goat Ig-FITC to control and specific goat anti-human Ig-FITC, at proper concentrations, to IgG, M and A tubes, respectively.
6. Incubate for 15–30 minutes in the dark.
7. Wash once with saline and add 1 mL to final volume.
8. Read on flow cytometer using Fwd Scatter versus Fl1.
9. Set positive region based on Control tube for that patient.

EXAMPLE 32

Ig Coating Procedure
1. Label three test tubes IgG, M, and A.
2. Place 1 mL of Carbonate buffer into each tube.
3. Place previously calculated amount of beads into each appropriate tube. (e.g. 4 µm into IgG, 5 µm into IgM, and 6 µm into IgA)
4. Gently vortex solution.
5. Centrifuge at full speed in a cold centrifuge for 5 minutes.
6. Decant supernatant and gently resuspend.
7. QS to 1 mL with carbonate buffer and vortex.
8. Add previously determined quantity of human Ig to each tube. (e.g. 10 µg of IgG to the 4 µm beads, 10 µg of IgM to the 5 µm beads, etc.).
9. Gently vortex solution and cover.
10. Incubate for 18–20 hours at 4–8 degrees C.
11. Gently invert 6 times to resuspend beads.
12. Centrifuge for 5 minutes, at full speed, in a refrigerated centrifuge.
13. Decant supernatant and gently resuspend.
14. QS to 1 mL with carbonate buffer.

The above procedure is for the production of 1 mL of bead reagent (Ig control material). Increased volumes may be made by multiplying the reagents by the factor of total volume needed.

EXAMPLE 33

Ig Positive Control Assay
1. Incubate Type C platelets with 100 µL of control or patient serum in tubes labeled Control, IgG, IgM and IgA.
2. After 15 minutes, wash tubes with 1 mL of saline.
3. Decant and gently vortex.
4. Add 100 µL of Ig control reagent from a previous example to each tube labeled IgG, IgM and IgA, respectively.
5. Add goat Ig-FITC to control and specific goat anti-human Ig-FITC, at proper concentrations, to IgG, IgM and IgA tubes, respectively.
6. Incubate for 15 minutes in the dark.
7. Wash once with saline and add 1 mL to final volume.
8. Read on flow cytometer using Fwd Scatter versus Fl1.
9. Set positive fluorescence region based on Control tube for that patient.

EXAMPLE 34

Platelet Ig Positive Control Reagent
1. Label three test tubes IgG, IgM, and IgA, respectively.
2. Place 1 mL of Carbonate buffer into each tube.
3. Place previously calculated amount of different sized µm beads into each appropriate tube. (e g. 4 µm into IgG, 5 µm into IgM, and 6 µm into IgA)
4. Gently vortex solution.
5. Centrifuge at full speed in a cold centrifuge for 5 minutes.
6. Decant supernatant and gently resuspend.
7. QS to 1 mL with carbonate buffer and vortex.
8. Add previously determined quantity of respective human Ig to each tube. (e.g. 10 µg of IgG to the 4 µm beads, 10 µg of IgM to the 5 µm beads, etc.).
9. Gently vortex solution and cover.
10. Incubate for 18–20 hours at 4–8 degrees C.
11. Gently invert 6 times to resuspend beads.
12. Centrifuge for 5 minutes, at full speed, in a refrigerated centrifuge.
13. Decant supernatant and gently resuspend.
14. QS to 1 mL with carbonate buffer.

The above procedure is for the production of 1 mL of each Ig bead reagent. Increased volumes may be made by multiplying the quantities by the factor of total volume needed.

EXAMPLE 35

Ig Positive Control Assay

Direct Procedure:

1. Add 100 μL of each of the Ig control coated beads of Example 36 to a respective tube labeled IgG, IgM and IgA.
2. Add goat Ig-FITC or goat anti-human Ig-FITC, at proper concentration, to each Control, IgG, IgM and IgA tube, respectively.
3. Incubate for 15 minutes in the dark.
4. Wash once with saline and add 1 mL to final volume.
5. Read on flow cytometer using Fwd Scatter versus FL1.
6. Set positive fluorescence region based on Control tube for that patient.

EXAMPLE 36

Ig Control Coated Beads

1. Label three test tubes IgG, IgM, and IgA.
2. Place 1 mL of Carbonate buffer into each tube.
3. Place previously calculated amount of selected μm beads into each appropriate tube. (e.g. 8 μm into IgG, 10 μm into IgM, and 12 μm into IgA)
4. Gently vortex solution.
5. Centrifuge at full speed in a cold centrifuge for 5 minutes.
6. Decant supernatant and gently resuspend.
7. QS to 1 mL with carbonate buffer and vortex.
8. Add previously determined quantity of respective human Ig to each tube. (e.g. 10 μg of IgG to the 8 μm beads, 10 μg of IgM to the 10 μm beads, etc.).
9. Gently vortex solution and cover.
10. Incubate for 18–20 hours at 4–8 degrees C.
11. Gently invert 6 times to resuspend beads.
12. Centrifuge for 5 minutes, at full speeds in a refrigerated centrifuge.
13. Decant supernatant and gently resuspend.
14. QS to 1 mL with carbonate buffer.

The above procedure is for the production of 1 mL of each Ig control coated bead reagent. Increased volumes may be made by multiplying the quantities by the factor of total volume needed.

EXAMPLE 37

Analyte Control Material

1. Label each test tube with a separate analyte to be tested.
2. Place 1 mL of Carbonate buffer into each tube.
3. Place previously calculated amount of a different sized, dyed, or shaped bead into each appropriate tube. (e.g. 4 μm into IgG, 5 μm into IgM, and 6 μm into IgA)
4. Gently vortex solution.
5. Centrifuge at full speed in a cold centrifuge for 5 minutes.
6. Decant supernatant and gently resuspend.
7. QS to 1 mL with carbonate buffer and vortex.
8. Add previously determined quantity of human Ig to each analyte in each tube. (e.g. 10 μg of IgG to the 4 μm beads, 10 μg of IgM to the 5 μm beads, etc.).
9. Gently vortex solution and cover.
10. Incubate for 18–20 hours at 4–8 degrees C.
11. Gently invert 6 times to resuspend beads.
12. Centrifuge for 5 minutes, at full speed, in a refrigerated centrifuge.
13. Decant supernatant and gently resuspend.
14. QS to 1 mL with carbonate buffer.

The above procedure is for the production of 1 mL of analyte control material Increased volumes may be made by multiplying the reagents by the factor of total volume needed.

EXAMPLE 38

Figure 33:
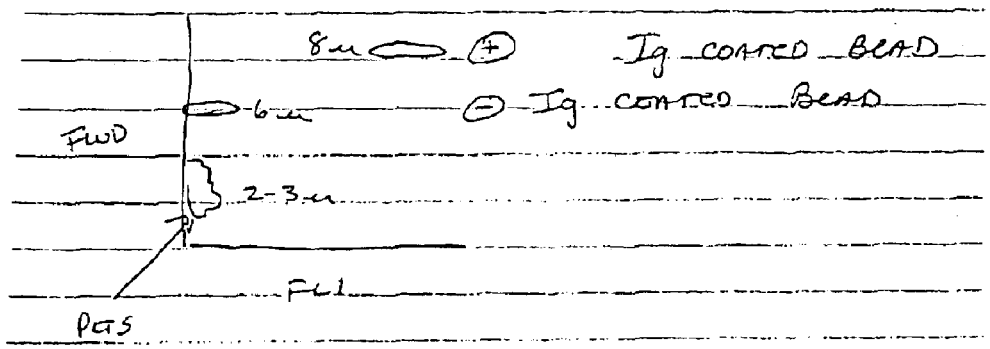

Platelet Evaluation Positive Control System (FIG. 33)

1. Coating of control beads (reagents) is the same as for the SLE kit but no 0.5% albumin wash.
2. Use three different bead sizes for three different human Ig's. Use one bead size for one human Ig.
3. Also, can use different sized beads for the coated and uncoated (+ and −) beads.
4. Use beads in screening for IgG, IgA, and IgM label same as SLE screen with specific goat anti-human IgG, IgA and IgM FITC conjugated antibody.

Thus it will be appreciated that, as a result of the present invention, a highly effective improved assay, reagent, control kit and system are provided by which the principal objective, among others, is completely fulfilled. It is contemplated, and will be apparent to those skilled in the art from the preceding description and accompanying drawings, that modifications and/or changes may be made in the illustrated embodiments without departing from the present invention. Accordingly, it is expressly intended that the foregoing description and accompanying drawings are illustrative of preferred embodiments only, not limiting, and that the true spirit and scope of the present invention be determined by reference to the appended claims.

TABLE I

Comparison of antibody detection by ELISA and Flow Cytometry (FC) Antibody Detected

| Result | nRNP | Sm | SSA | SSB | Scl-70 |
|---|---|---|---|---|---|
| Positive by ELISA and FC | 70 | 21 | 95 | 23 | 15 |
| Negative by ELISA and FC | 232 | 282 | 203 | 281 | 277 |
| Positive by ELISA Negative by FC | 11 | 15 | 6 | 12 | 25 |
| Negative by ELISA Positive by FC | 8 | 3 | 17 | 5 | 4 |
| Number of Samples | 321 | 321 | 321 | 321 | 321 |
| OverallAgreement | 94% | 94% | 93% | 95% | 91% |

This table summarizes the results of a comparison between an ELISA method and the Flow Cytometry method for detecting antibodies to nRNP, Sm, SSA, SSB, and Scl-70. It indicates the number of samples that gave the specified result for the antibody detected as well as the overall agreement of the two methods. Overall agreement is equal to (Positive by ELISA and FC+Negative by ELISA and FC)/Number of Samples.

What is claimed is:

1. An immunobead platelet assay using flow cytometry comprising the steps of:

preparing IgG, IgM and IgA coated bead based Ig control reagent by adding a bead coated with IgG or subclasses thereof to an IgG test set comprising a test tube labeled IgG and an IgG control tube, adding a bead coated with IgM or subclasses thereof to an IgM test set comprising a test tube labeled IgM and an IgM control tube, adding a bead coated with IgA or subclasses thereof to an IgA test set comprising a test tube labeled IgA and an IgA control tube, wherein an assay has a least two test sets;

adding patient platelets to each test tube labeled IgG, IgM and IgA respectively and adding Type O control platelets to each of the IgG, IgM and IgA control tubes;

adding fluorochrome conjugated species specific Ig to each of the IgG, IgM and IgA control tubes, and fluorochrome conjugated species specific anti-human IgG, IgM and IgA to each of the test tubes labeled IgG, IgM and IgA respectively;

incubating the tubes for 15 minutes in the dark;

washing once with isotonic saline and adding additional isotonic saline to a final volume, and reading each tube on a flow cytometer to analyze the contents thereof.

2. An immunobead platelet assay using flow cytometry comprising the steps of:

preparing IgG, IgM and IgA coated bead based Ig control reagent by adding a bead coated With IgG or subclasses thereof to an IgG test set comprising a test tube labeled IgG and/or an IgG control tube, adding a bead coated with IgM or subclasses thereof to an IgM test set comprising a test tube labeled IgM and/or an IgM control tube, adding a bead coated with IgA or subclasses thereof to an IgA test set comprising a test tube labeled IgA and/or an IgA control tube, wherein an assay has a least two test sets;

adding type O platelets to all of the tubes;

incubating Type O platelets in the IgG, IgM and IgA control tubes by adding a control serum to the IgG, IgM and IgA control tubes, and incubating the type O platelets in the IgG, IgA and IgM control tubes by adding a patient serum to the IgG, IgA and IgM control tubes and the test tubes labeled IgG, IgA and IgM;

washing each of the tubes with isotonic saline, decanting and gently vortexing;

adding fluorochrome conjugated species specific Ig to each of the IgG, IgM and IgA control tubes, and fluorochrome conjugated species specific anti-human IgG, IgM and IgA to each of the test tubes labeled IgG, IgM and IgA respectively;

incubating the tubes in the dark;

washing once with saline and adding additional saline to final volume, and reading each tube on a flow cytometer to analyze the contents thereof.

3. The assay as recited in claim 1 further comprising the steps of:

placing at least 1 mL of carbonate buffer into each tube;

placing an amount of a different sized bead into each tube to form a bead solution;

gently vortexing the bead solution in each tube;

centrifuging at full speed in a cold centrifuge for about 5 minutes;

decanting supernatant and gently suspending;

filling to 1 mL with carbonate buffer and vortexing;

adding a quantity of a different human Ig selected from IgG, IgM and IgA to each tube to form a solution;

gently vortexing the solution in each tube and covering;

incubating for about 18–20 hours at 4–8° C.;

gently inverting 2–6 times to resuspend beads;

centrifuging for about 5 minutes a full speed, in a refrigerated centrifuge;

decanting supernatant and gently suspending, and filling to about 1 mL with carbonate buffer.

4. The assay as recited in claim 2 wherein said bead based Ig control reagent is made by a process comprising the steps of:

labeling three test-tubes IgG, IgM and IgA respectively;

placing about 1 mL of carbonate buffer into each tube;

placing an amount of a different sized bead into each separate tube to form a bead solution;

gently vortexing the bead solution in each tube;

centrifuging at full speed in a cold centrifuge for about 5 minutes;

decanting supernatant and gently suspending;

filling to 1 mL with carbonate buffer and vortexing;

adding a quantity of a different human Ig selected from IgG, IgM and IgA to each tube to form a solution;

gently vortexing the solution in each tube and covering;

incubating for about 18–20 hours at 4–8° C.;

gently inverting 2–6 times to resuspend beads;

centrifuging for about 5 minutes at full speed, in a refrigerated centrifuge;

decanting supernatant and gently suspending, and filling to about 1 mL with carbonate buffer.

5. An immunobead platelet assay using flow cytometry, comprising the steps of:

preparing eight tubes comprising first and second Ig tubes, first and second IgG tubes, first and second IgA tubes and first and second IgM tubes, each of the first tubes being for normal patient control, and each of the second tubes being for the patient being tested;

adding patient platelets to each tube;

adding to the first Ig tube a volume of $X\mu$ beads with human IgG attached, a volume of $X\mu$ beads with human IgA attached, and a volume of $X\mu$ beads with human IgM attached;

adding to the first IgG tube a volume of $X\mu$ beads with human IgG, adding to the first IgA tube a volume of $X\mu$ beads with human IgA, and adding to the first IgM tube a volume of $X\mu$ beads with human IgM;

adding to the second Ig tube a species specific isotypic control that has been fluorescently conjugated;

adding to the second IgG tube a species specific conjugated anti-human IgG, adding to the IgA tube a species specific conjugated anti-human IgA, and adding to the IgM tube a species specific conjugated anti-human IgM;

vortexing and incubating all of the tubes for a given amount of time;

washing the contents of each tube with isotonic saline;

decanting supernatant, gently vortexing and resuspending the contents of each tube in isotonic saline; and reading each tube from a flow cytometer to analyze the contents thereof.

6. An assay as claimed in claim 5 wherein the $X\mu$ beads comprise $6\mu$ beads.

7. An immunobead platelet assay using flow cytometry comprising the steps of:

preparing eight tubes comprising first and second Ig tubes, first and second IgG tubes, first and second IgA tubes and first and second IgM tubes, each of the first tubes being for normal patient control, and each of the second tubes being for the patient being tested;

adding type O platelets to each of the tubes;

adding normal serum to each of the first tubes for a normal control set;

adding patient serum to each of the second tubes for a patient control set;

vortexing and incubating all tubes;

adding isotonic saline and vortexing the contents of all tubes;

centrifuging the contents of all tubes, removing supernatant and decanting thereof;

adding to the first Ig tube a volume of X$\mu$ beads with human IgG attached, a volume of X$\mu$ beads with human IgA attached, and a volume of X$\mu$ beads with human IgM attached;

adding to the first IgG tube a volume of X$\mu$ beads with human IgG, adding to the first IgA tube a volume of X$\mu$ beads with human IgA, and adding to the first IgM tube a volume of X$\mu$ beads with human IgM;

adding to the second Ig tube a species specific isotypic control that has been fluorescently conjugated;

adding to the second IgG tube a species specific conjugated anti-human IgG, adding to the IgA tube a species specific conjugated anti-human IgA, and adding to the IgM tube a species specific conjugated anti-human IgM;

vortexing and incubating all of the tubes for a given amount of time;

washing the contents of each tube with isotonic saline;

decanting supernatant, gently vortexing and resuspending the, contents of each tube in isotonic saline; and reading each tube from a flow cytometer to analyze the contents thereof.

* * * * *